(12) United States Patent
Cai

(10) Patent No.: US 10,267,808 B2
(45) Date of Patent: Apr. 23, 2019

(54) MOLECULAR INDICIA OF CELLULAR CONSTITUENTS AND RESOLVING THE SAME BY SUPER-RESOLUTION TECHNOLOGIES IN SINGLE CELLS

(75) Inventor: Long Cai, Port Jefferson Station, NY (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 13/043,413

(22) Filed: Mar. 8, 2011

(65) Prior Publication Data
US 2012/0142014 A1 Jun. 7, 2012

Related U.S. Application Data

(60) Provisional application No. 61/311,654, filed on Mar. 8, 2010.

(51) Int. Cl.
| C12Q 1/68 | (2018.01) |
| G01N 33/68 | (2006.01) |
| C12Q 1/6841 | (2018.01) |

(52) U.S. Cl.
CPC ....... *G01N 33/6872* (2013.01); *C12Q 1/6841* (2013.01)

(58) Field of Classification Search
USPC .......... 435/6.1, 6.11, 7, 1, 91.1, 83; 436/94, 436/501; 536/23.1, 24.3, 24.33
See application file for complete search history.

(56) References Cited

U.S. PATENT DOCUMENTS

| 5,866,331 | A | 2/1999 | Singer et al. |
| 6,242,184 | B1* | 6/2001 | Singer et al. ................ 435/6.14 |
| 6,534,266 | B1* | 3/2003 | Singer .............................. 506/4 |
| 2003/0064025 | A1 | 4/2003 | Yang et al. |
| 2003/0152490 | A1 | 8/2003 | Trulson et al. |
| 2003/0170613 | A1 | 9/2003 | Straus |
| 2004/0171076 | A1 | 9/2004 | Dejneka et al. |

(Continued)

FOREIGN PATENT DOCUMENTS

| WO | WO2011112634 | 9/2011 |
| WO | WO2012058638 | 5/2012 |

OTHER PUBLICATIONS

Andrea et al., Visualization of Single RNA Transcripts in Situ. Science, 280, 585-590, Apr. 24, 1998.*
(Continued)

*Primary Examiner* — Frank W Lu
(74) *Attorney, Agent, or Firm* — Squire Patton Boggs (US) LLP

(57) ABSTRACT

Methods and systems are provided for creating molecular barcodes or indicia for cellular constituents within single cells and for resolving such barcodes or indicia with super resolution technologies such as super resolution microscopy. By this approach, numerous molecular species that can be measured simultaneously in single cells. It has been demonstrated that multiple mRNA transcripts can be labeled with a spatially ordered sequence of fluorophores, and that barcode can be resolved. The methods and systems can be used for genome-wide transcriptional profiling in individual cells by super-resolution barcoding and suggest a general strategy to bring large-scale-omics approach into single cells.

13 Claims, 16 Drawing Sheets

(56) References Cited

U.S. PATENT DOCUMENTS

| | | |
|---|---|---|
| 2004/0229253 A1 | 11/2004 | Hydig-Nielsen et al. |
| 2004/0253593 A1 | 12/2004 | Cai et al. |
| 2005/0059681 A1 | 3/2005 | Cremer et al. |
| 2010/0304994 A1 | 12/2010 | Wu et al. |
| 2014/0031243 A1 | 1/2014 | Cai et al. |
| 2014/0073520 A1 | 3/2014 | Cai et al. |

OTHER PUBLICATIONS

Donnert et al., Macromolecular-scale resolution in biological fluorescence microscopy. PNAS, 103, 11440-11445, 2006.*
Table of Fluorochromes. Printed on Aug. 19, 2012.*
What Wavelngth Goes with a Color. Printed on Aug. 19, 2012.*
Lu et al., Quantification of miRNA Abundance in Single Cells Using Locked Nucleic Acid-FISH and Enzyme-Labeled Fluorescence. Methods in Molecular Biology 680,77-88, 2010.*
Yildiz et al., Fluorescence Imaging with One Nanometer Accuracy: Application to Molecular Motors. Acc. Chem. Res. 38, 574-582, 2005.*
Rust et al., Sub-diffraction-limit imaging by stochastic optical reconstruction microscopy (STORM). Nature Method, 3, 793-795, 2006.*
ISR-WO from PCT/US2011/027618, dated Jan. 2, 2012.
Written Opinion—WO from PCT/US2011/027618, dated Jan. 2, 2012.
Fernandez-Suarez, M. et al., Nature Reviews Dec. 2008, vol. 9, pp. 929-944.
Lubeck et al., Single-Cell Systems Biology by Super-Resolution Imaging and Combinatorial Labeling, Nature Methods, vol. 9, No. 7, Jul. 2012.
Levsky et al., Single-Cell Gene Expression Profiling, Science, vol. 297, Aug. 2, 2002.
Blanco et al. A FRET-based assay for characterization of alternative splicing events using peptide nucleic acid fluorescence in situ hybridization. Nucleic Acids Research (2009). 37(17): e116; 11 pages.
Schrock et al. Multicolor Spectral Karyotyping of Human Chromosomes. Science (1996). 273:494-497.

* cited by examiner

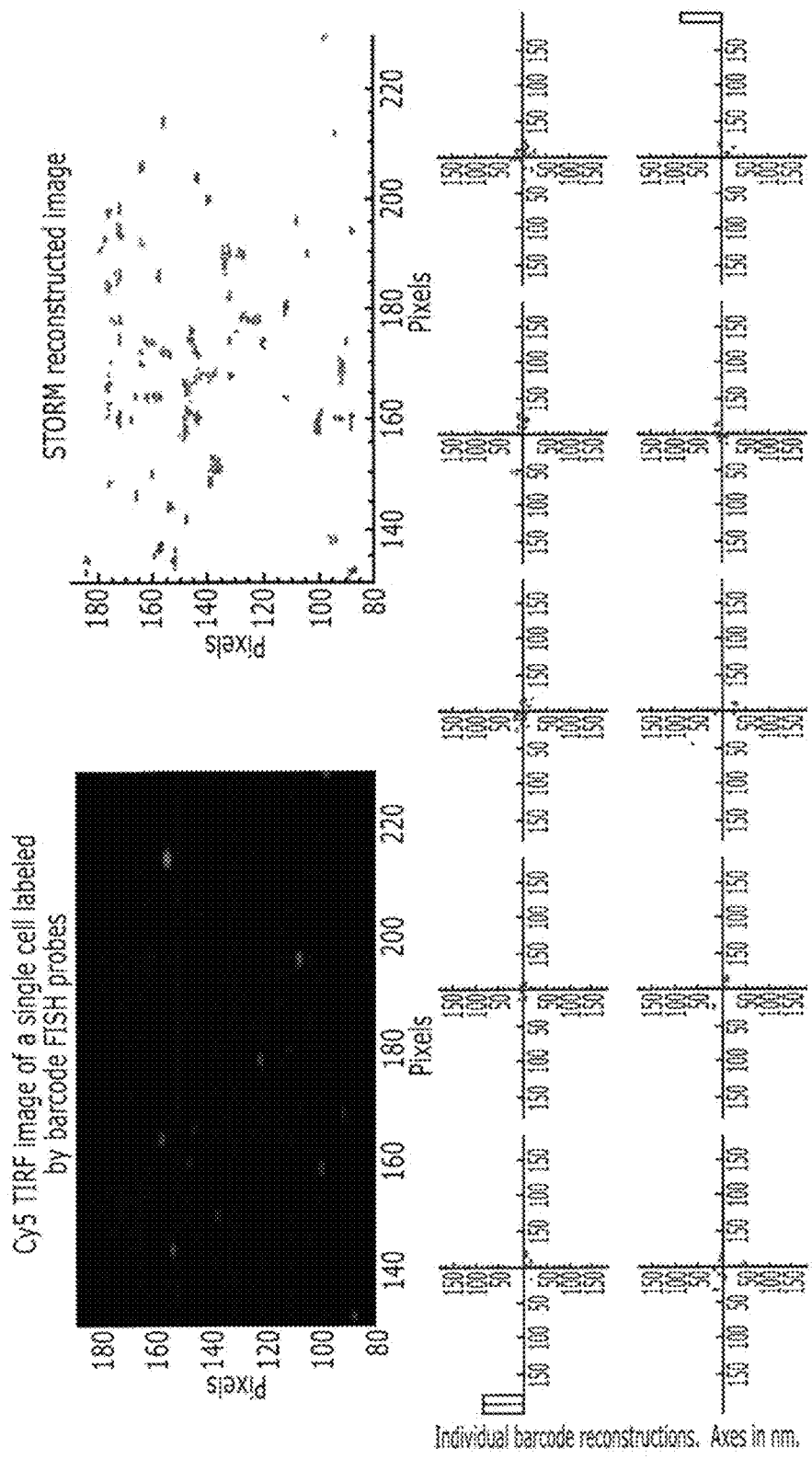

Individual barcode reconstructions. Axes in nm.

| Figure 7B-1 |
| Figure 7B-2 |

MOLECULAR INDICIA OF CELLULAR CONSTITUENTS AND RESOLVING THE SAME BY SUPER-RESOLUTION TECHNOLOGIES IN SINGLE CELLS

CROSS-REFERENCE TO RELATED APPLICATIONS

This application claims priority from U.S. Provisional Patent Application No. 61/311,654, filed on Mar. 8, 2010, which is incorporated herein by reference in its entirety.

STATEMENT REGARDING FEDERALLY-SPONSORED RESEARCH

This invention was made with government support under grant no. GM087588 awarded by National Institutes of Health. The U.S. Government has certain rights in the invention.

FIELD OF THE INVENTION

The invention disclosed herein generally relates to methods and systems that analyze biological systems in microscopic and macroscopic scales at the same time. Specifically, the invention disclosed herein relates to methods and systems that combine the power and advantages of genomics and single cells analyses. More specifically, the invention disclosed herein relates to methods and systems that encode cellular constituents with indicia based on genomics and then employ powerful tools such as super resolution microscopes that can resolve such indicia.

BACKGROUND

Advances in genomic research have revolutionized the fields of biology, genetics, and biochemistry. In particular, microarray technologies have enabled the study of molecular interactions at a large scale. As the collective understanding of biological systems progress, it is increasingly important that molecular interactions are understood both macroscopically and microscopically in a systematic fashion.

As a field of study, system biology is the study of the interactions between the components of biological systems, and how these interactions give rise to the function and behavior of that system (for example, the enzymes and metabolites in a metabolic pathway).

Current tools for macroscopic and systematic analyses of biological systems require tremendous input in both resource and manpower. What is needed in the art are methods and systems that can carry out such analyses with more efficiency and economy.

SUMMARY OF THE INVENTION

In one aspect, the present invention provides a method for creating a molecular indicium for a cellular constituent in a cell. The method comprises the steps of i) associating, within the cell, a quantity of a cellular constituent with a plurality of probes, wherein each of the plurality of probes is attached with a label that is capable of emitting a signal, and ii) creating, while said plurality of probes is associated with said quantity of the cellular constituent, a molecular indicium that can be used to identify a biological state of the cellular constituent or of said cell; wherein said indicium corresponds to signals emitted from the labels associated with the plurality of probes and is resolvable by separating signals from labels attached to said plurality of probes, using a super resolution technology at a resolution that is at 25 nm or better.

In some embodiments, the resolution of the technology can vary depending on the purposes for which the invention is used.

In another aspect, the method further comprises a step of resolving signals from labels attached to the plurality of probes by using super resolution technologies.

In another aspect, the method further comprises a step of attaching a label to one or more probes of said plurality of probes.

In another aspect, the method further comprises a step of selecting said plurality of probes based on a characteristic of said cellular constituent, wherein said characteristic is selected from the group consisting of sequence, size, abundance level, activity level, two-dimensional structure, three-dimensional structure, charged state, surface accessibility, location within the cellular context, binding affinity and specificity to another cellular constituent, and a combination thereof.

In some embodiments, the cell is essentially intact or undisrupted.

In some embodiments, the cell is a prokaryotic cell or a eukaryotic cell.

In some embodiments, the cell can be, for example, a bacterium, an archaea, a protist, a fungus, a plant cell, an animal cell, a mammalian cell, a mouse cell, a human cell, a cancer cell, a blood cell, a lymphocyte, an erythrocyte, a white blood cell, an epithelial cell, a pituitary cell, a gut or respiratory tract cell, a gland cell, a thyroid gland cell, a parathyroid gland cell, a adrenal gland cell, a muscle cell, a ciliated cell, an embryonic cell, a sensory transducer cell, a neuron, a glial cell, a lens cell, a kidney cell, a pigment cell, a pancreatic cell, or combinations thereof.

In some embodiments, the cellular constituent is an mRNA, a DNA, a protein, or a hybrid thereof.

In some embodiments, the plurality of probes comprises oligonucleotides tiled along the sequence of an mRNA transcript.

In some embodiments, the plurality of probes comprises probes that bind to the same cellular constituent.

In some embodiments, the plurality of probes binds to different parts of the same cellular constituent.

In some embodiments, the plurality of probes comprises probes that bind to at least two different cellular constituents.

In some embodiments, the label is a fluorescent label.

In some embodiments, the fluorescent label is attached to the plurality of probes via an intermediary composition.

In some embodiments, the intermediary composition is a DNA or derivatives thereof, an RNAs or derivatives thereof, a DNA-RNA hybrids or derivatives thereof, or a peptide or analogs thereof.

In some embodiments, the fluorescent label can be, for example, fluorescein, rhodamine, Alexa Fluors, DyLight fluors, ATTO Dyes, or any analogs or derivatives thereof.

In some embodiments, the fluorescent label can be, for example, fluorescein and chemical derivatives thereof, Eosin, Carboxyfluorescein, Fluorescein isothiocyanate (FITC), Fluorescein amidite (FAM), Erythrosine, Rose Bengal, fluorescein secreted from the bacterium *Pseudomonas aeruginosa*, Methylene blue, Laser dyes, Rhodamine dyes, Rhodamine, Rhodamine 6G, Rhodamine B, Rhodamine 123, Auramine O, Sulforhodamine 101, Sulforhodamine B, Texas Red, ATTO dyes, Acridine dyes, Acridine orange, Acridine yellow, Alexa Fluor, 7-Aminoactinomycin D, 8-Anilinonaphthalene-1-sulfonate, Auramine-rhodamine stain, Benzanthrone, 5,12-Bis(phenylethynyl)naphtacene, 9,10-Bis(phenylethynyl)anthracene, Blacklight paint, Brainbow, Calcein, Carboxyfluorescein, Carboxyfluorescein diacetate succinimidyl ester, Carboxyfluorescein succinimidyl ester, 1-Chloro-9,10-bis(phenylethynyl)anthracene, 2-Chloro-9,10-bis(phenylethynyl)anthracene, 2-Chloro-9,10-diphenylanthracene, Coumarin, Cyanine dyes, Cy3, Cy5, Cy5.5, DiOC6, SYBR Green I, DAPI, Dark quencher, DyLight Fluor, Fluo-4, FluoProbes, Fluorone dyes, Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin, Fluoro-Jade stain, Fura-2, Fura-2-acetoxymethyl ester, Green fluorescent protein, Hoechst stain, Indian yellow, Indo-1, Lucifer yellow, Luciferin, Merocyanine, Optical brightener, Oxazin dyes, Cresyl violet, Nile blue, Nile red), Perylene, Phenanthridine dyes, Ethidium bromide, Propidium iodide, Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate)ruthenium(II), TSQ, Umbelliferone, or Yellow fluorescent protein.

In some embodiments, the resolvable indicium is a linear, two-dimensional or three-dimensional pattern of signals emitted from labels associated with the plurality of probes.

In some embodiments, the signals emitted from labels associated with said plurality of probes comprise a light at a wavelength in the visible range.

In some embodiments, the signals emitted from labels associated with said plurality of probes comprise lights of different wavelengths in the visible range.

In some embodiments, the plurality of probes comprises oligo nucleotides, peptides, or antibodies.

In some embodiments, the biological state is selected from the group consisting of copies of mRNA transcripts associated with a particular gene, a location of gene transcript within a cell, sequence, size, abundance level, activity level, two-dimensional structure, three-dimensional structure, charged state, surface accessibility, location within the cellular context, binding affinity and specificity to another cellular constituent, or a combination thereof.

In some embodiments, the super resolution technology can be, for example, Stimulated Emission Depletion microscopy (STEDM), Ground State Depletion microscopy (GSDM), Spatially Structured Illumination microscopy (SSIM), Total Internal Reflection Fluorescence Microscope (TIRFM) Photo-Activated Localization Microscopy (PALM), Fluorescence-PALM (FPALM), Stochastical Optical Reconstruction Microscopy (STORM), Fluorescence Imaging with One-Nanometer Accuracy (FIONA), or combinations thereof.

In another aspect, the method also comprises the step of determining said biological state of said cellular constituent or said cell based on said indicium.

In another aspect, the present invention provides a system for analyzing a cellular constituent in a cell. The system comprises a plurality of probes that can be associated with a quantity of a cellular constituent within the cell, wherein each of the plurality of probes is attached with a label that is capable of emitting a signal, and wherein the signals emitted from labels associated the plurality of probes create an indicium that can be used to identify a biological state of the cellular constituent or the cell; and an imaging equipment employing super resolution technology at a resolution that is at 25 nm or better.

BRIEF DESCRIPTION OF THE DRAWINGS

Those of skill in the art will understand that the drawings, described below, are for illustrative purposes only. The drawings are not intended to limit the scope of the present teachings in any way.

FIGS. 2A-2H depict exemplary embodiments, demonstrating spatial order on transcripts resolved by FIONA. A) Fluorescence images of FISH in each dye channel. Two fluorescent spots are highlighted in each channel for further display. B) Probe Schematic. 3 sets of oligo probes labeled with different fluorophores are hybridized to YLR414c mRNA. C) Reconstructions of the centroid of spots 1 and 2 following localizations by Gaussian fitting. D) The percentage of co-localized three-color PSFs that can be reconstructed with a correct barcode. E) Schematic of probeset hybridized to GFP mRNA with changed order and distances between the probes. F) FIONA reconstruction from this probe set. G) The frequency of the order of barcode resolved from this probe set. H) The spatial distance distribution between the resolved centroids positions reflect the molecular distance between barcode positions.

DETAILED DESCRIPTION OF THE INVENTION

Definitions

Figures 1A, 1B, 1C, 1D:
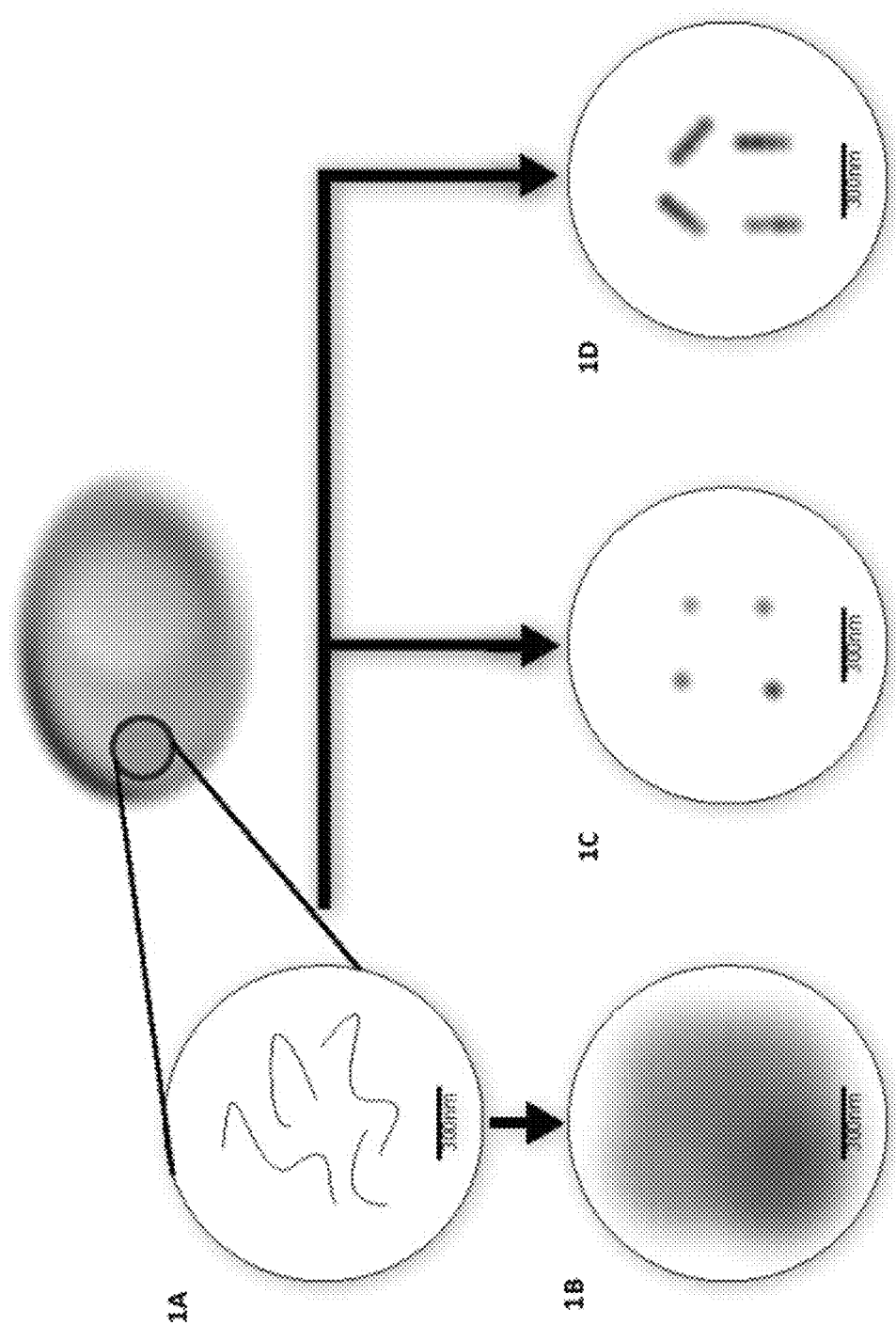
FIGS. 1A-1G depict exemplary embodiments, demonstrating that super-resolution and combinatorial molecular labeling allows high-throughput multiplex detection of molecular species in single cells. A-B) Molecular species in cells are difficult to resolve by conventional microscopy due to the diffraction limit of 300 nm. C) Super-resolution microscopy allows spatial resolution of individual molecules. D) The different species of molecules can be uniquely identified by a super-resolution barcode imparted by molecular labeling. SRM resolution of $(10\text{ nm})^3$ allows a typical cell of $(10\text{ um})^3$ to be decomposed into $10^9$ pixels, more than sufficient to accommodate the 106 copies of transcripts in a typical transcriptome. mRNA can be combinatorial labeled by FISH probes. A transcriptome of $10^4$ distinct mRNA species can be covered by a 6-position barcode with 6 fluorophores. 1E depict an exemplary embodiment, demonstrating transcriptional profiling in single cells by super-resolution barcoding. Single molecules of mRNA (grey) can be visualized as dots in the cell by FISH. Each species of mRNA is barcoded by a set of labeled sequence-specific oligo probes; example shown in color. The copy number of each species of mRNA can be quantified by counting the number of occurrences of each barcode in the cell. A transcriptome of $10^4$ distinct mRNA species can be covered by a 6-position barcode with 6 fluorophores. F) and G) illustrate intensity coding and spatial coding, respectively.

Unless otherwise noted, terms are to be understood according to conventional usage by those of ordinary skill in the relevant art.

As used herein, the term "an essentially intact or undisrupted cell" refer to a cell that is completely intact or largely conserved with respect to its macromolecular cellular content. For example, a cell within the meaning of this term can include a cell that is made at least partially permeable such that external buffer and reagents can be introduced into the cell. Such external reagents include but are not limited to probes, labels, labeled probes, and/or combinations thereof.

As used herein, the term "cellular constituent" refers to any measurable biological variables that can be used in accordance with the present invention. Exemplary cellular constituents include but are not limited to any large biomolecules such as a DNA molecule or a fragment thereof, an RNA molecule or a fragment thereof, an mRNA molecule or a fragment thereof, a protein molecule or a fragment thereof, an mRNA complex or a section thereof, a protein complex or a section thereof, an organelle or a section thereof, or combinations thereof. Exemplary properties of cellular constituents include but are not limited to abundance level, location within a cell, abundance level or location with respect to other cellular constituents, relation to other cellular constituents, etc.

As used herein, the term "indicia" or "indicium" refers to any method, composition or system that can be associated with one or more cellular constituents to characterize at least one property of a cellular constituent at issue. As used herein, the term "molecular barcode" or "barcode" is used interchangeably with the term "indicium" or "indicia." The process of creating the indicia or barcode can be referred to as a barcoding process.

As used herein, the term "probe" refers to any composition that can be specifically associated with a target cellular constituent within a cell. A probe can be a small molecular or a large molecule. Exemplary probes include but are not limited to nucleic acids such as oligos, peptides, proteins (such as antibodies), or hybrids thereof.

As used herein, the term "label" refers to any composition that can be used to generate the signals that constitute an indicium. The signals generated by a label can be of any form that can be resolved subsequently to constitute the indicium. Preferably, the signal is a light within the visible range. In some embodiments, the signal is a light not in the visible range. In some embodiments, the signal is a radio signal, an X-ray signal, or an electro-magnetic signal. However, it will be understood by one of skill in the art that equipment and devices are available for recording and monitoring light of any wavelength.

As used herein, the term "biological state" is broadly defined to refer to a state, a characteristic, or a property that is associated with a cellular constituent. For example, it can be the number of copies of mRNA transcripts associated with a particular gene and the locations of these transcripts within a cell. It can also be the identity and location of other cellular constituents that interact or bind to the target cellular constituents. Exemplary biological states include but are not limited to sequence, size, abundance level, activity level, two-dimensional structure, three-dimensional structure, charged state, surface accessibility, location within the cellular context, binding affinity and specificity to another cellular constituent, or a combination thereof.

Two sets of orthogonal systems biology approaches, large scale and small scale techniques, have traditionally been undertaken to elucidate the cellular interactions and biochemical networks. The large scale systems approaches, exemplified by microarrays and sequencing techniques, can profile comprehensively the transcriptional and the genomic state of a population of cells. On the other hand, the small scale systems approaches, for example, those using fluorescence microscopy techniques, can examine key genetic and regulatory interactions in individual cells while preserving the spatial context of the interactions.

The present invention combines the advantages of both approaches to bring the power of genomics into single cells. In one aspect, the methods and systems described herein provide unprecedented resolution in molecular interactions occurring in biological networks. In one aspect, the methods and systems described herein provide important clinical tools in identifying molecular signatures of disease. In another aspect, the methods and systems described herein can revolutionize the day-to-day experimental routines in the field of biological sciences, including but not limited to cell biology, molecular biology, biochemistry, biophysics and chemistry.

One of skill in the art would understand that methods and systems described herein are applicable to all types of cells, including but not limited to bacteria, archaea, protists, fungi, plant, and animal cells, especially mammalian cells, mouse cells, human cells. Exemplary human cells include but are not limited to cancer cells, blood cells, lymphocytes, erythrocytes, white blood cells, epithelial cells, pituitary cells, gut and respiratory tract cells, various gland cells (e.g., thyroid, parathyroid, or adrenal glands), muscle cells, ciliated cells, embryonic cells, sensory transducer cells, various neuron cells, glial cells, lens cells, kidney cells, pigment cells, pancreatic cells, combinations thereof, etc.

Molecular Barcode

In one aspect, the power of genomics is brought into single cells via the creation of molecular barcodes or indicia, where barcodes or indicia are associated with specific cellular constituents.

Taking the high-throughput approach into a single cell may enable powerful exploration in many biological systems. However, multiplex detection of molecular species in single cells faces several fundamental challenges. First, individual cells need to be isolated. Then, molecules within those cells need to be separated, identified and quantified. Optical microscopy circumvents the need to isolate individual cells, but limits molecular discrimination, as molecules cannot be resolved beyond the diffraction limit (~300 nm). Referring to FIGS. 1A-1D, super-resolution technologies such as super-resolution microscopy (SRM) bypasses the diffraction limit and allows the location of individual molecules to be determined accurately within 10-20 nm. This implies that under a super-resolution microscope with a 10 $nm^3$ resolution, a typical cell of 10 $um^3$ is composed of $10^9$ pixels. In comparison, there are only $10^6$ transcripts present in most cells. Thus, distinct molecules can be spatially resolved natively within the cell under SRM. Then, their identities can be uniquely addressed by combinatorial barcode labeling that is resolvable in super-resolution imaging (FIG. 1D). A 6 color 6 position barcode ($6^6/2=23,328$) is sufficient to uniquely code for each transcript in a mammalian transcriptome. In this fashion, SRM and combinatorial molecular labeling provide a general strategy to quantify molecular species on a genomic scale with single molecule precision in single cells.

The present methods and systems of molecular barcoding are used to illustratively detect multiple mRNA species in single Saccharomyces cerevisiae cells (Table 1).

As described above, a molecular barcode is broadly defined as a form of indicia that can be used to determine the identity or any other characteristics and/or properties of a cellular constituent in a cell. The methods and systems described herein can be used for research, diagnostic, prognostic or any other purposes. The cell can be a prokaryotic cell or a eukaryotic cell. For example, barcoding can be done in simple model organisms such as E. coli or yeast to monitor and study processes that include but are not limited to transcription, translation, protein folding, and protein-trafficking. Alternatively, methods and systems of barcoding can be used in more advanced organisms such as animal and human cells, for example, to determine a complicated structure of molecular complexes, to dissect a signaling pathway, or to monitor and quantify changes within the cells.

In some embodiments, a molecular barcode or indicium comprises a visual component, for example, in the form of a combination of different visible colors affixed to labels that are in turn affiliated with probes bound to one or more target cellular constituents in a cell. In some embodiments, the color type and frequency of these labeled probes are used to create a molecular barcode.

Figure 1E:
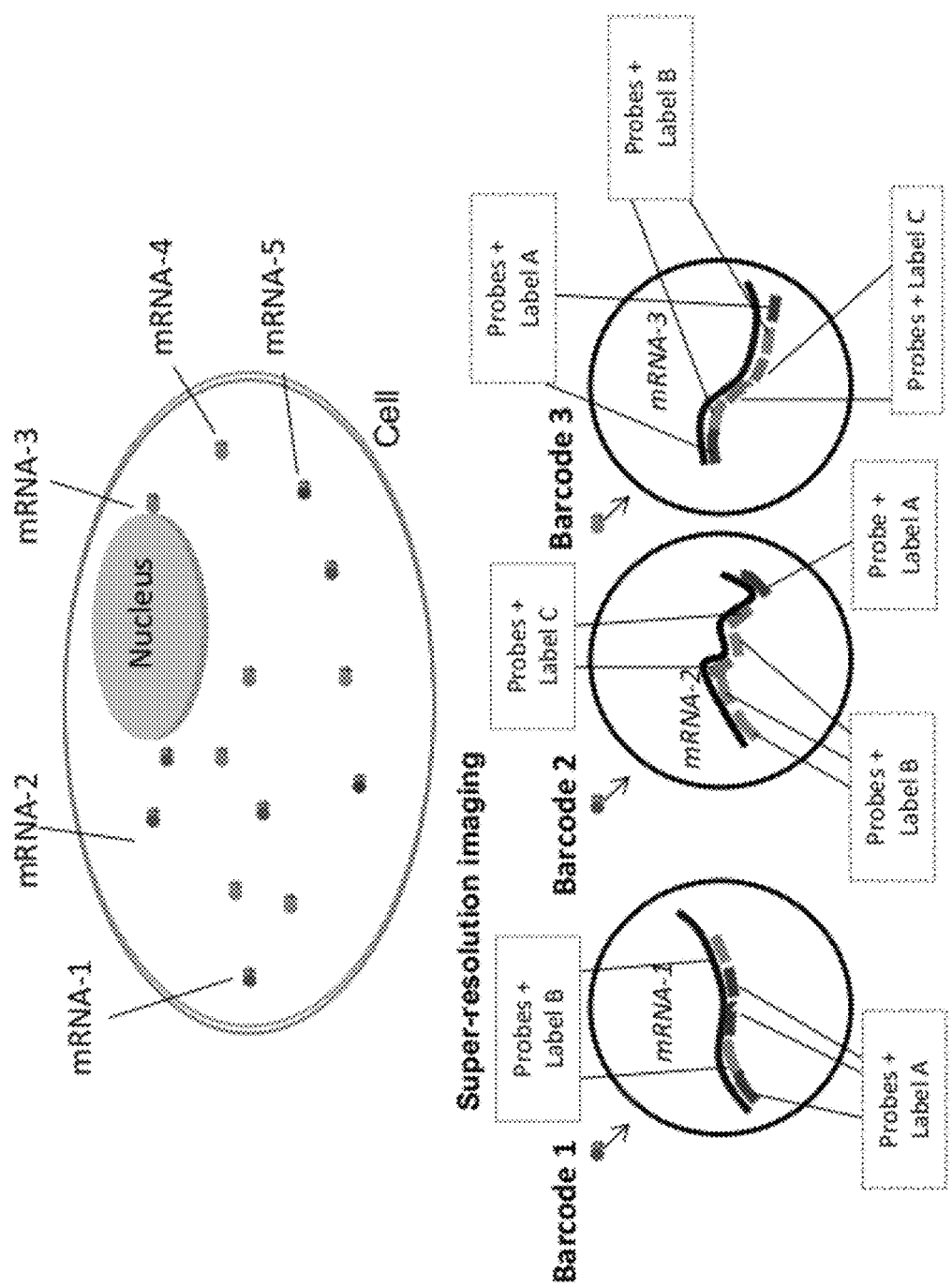

Referring to FIG. 1E, a schematic representation of a single cell is shown with several labeled mRNA transcripts, e.g., mRNA-1 through mRNA-5. Each transcript is observed as being associated with a different indicium, when being subjected to super resolution imaging. For example, mRNA-1 appears purple; mRNA-2 appears green; and mRNA-3 appears orange. Here, each mRNA transcript is associated with a unique molecular barcode. The present invention enables simultaneous counting of multiple mRNA species with single molecule sensitivity in a single cell. Single molecules of mRNA (grey) can be visualized as dots in the cell. Each species of mRNA is barcoded by a unique set of labeled sequence specific oligo probes; example shown in color. The barcode can be resolved by STORM with a resolution of 5 nm. The copy number of each species of mRNA can be quantified by counting the number of occurrences of ach barcode in the cell. A transcriptome of $10^4$ distinct mRNA species can be entirely covered by a 6-position barcode with 6 STORM dye colors.

Exemplary barcodes associated with transcripts mRNA-1, mRNA-2 and mRNA-3 are described further to illustrate the concept of molecular barcoding. In particular, barcode 1, which corresponds to mRNA-1 transcript, comprises five oligo nucleotide probes that each bind to a specific segment of the mRNA-1 transcript, including three probes with label A and two probes with label B. In this example, label A is red and label B is blue. The combined effect of three blue labels and two copies of red label is depicted as purple-like color and revealed by super resolution imaging to correspond to an arrangement of Red-Blue-Red-Red-Blue. In a different example, one probe with red label A, three probes with blue label B and two probes with green label C constitute barcode 2, which is used to represent mRNA-2. Barcode-2 is read under super resolution imaging to correspond to an arrangement of Blue-Blue-Green-Blue-Green-Red. In still another example, Barcode-3 is read under super resolution imaging to correspond to an arrangement of Red-Blue-Green-Green-Blue-Red.

As illustrated above, the types of signals (e.g., color) associated with each probe, the frequency and arrangement of these labeled probes can all be used to define a molecular barcode. Although no obvious gaps are present in the exemplary barcodes in FIG. 1, one of skill in the art would understand that absence of any signal (e.g., color) in parts of a cellular constituent can also be used to define a molecular barcode.

In some embodiments, in addition to the more or less linear order arrangements described above, more complex arrangements of the colored probes can also be used to define a molecular barcode associated with a particular cellular constituent. Exemplary non-linear arrangements include, for example, two-dimensional grids, maps, or three-dimensional lattices.

In some embodiments, for a less linear cellular constituent such as a protein, more complex spatial arrangements are needed to create the corresponding molecular barcode. For example, labeled antibodies targeting surface epitopes can be used to create one or more maps that uniquely identify the protein at issue. One of skill in the art would understand that a molecular barcode for a protein relies on knowledge of the structure of the protein at issues, the distribution of surface epitopes, as well as the availability of antibodies targeting such surface antibodies.

In some embodiments, small synthetic antibodies are used as probes when targeting one or more proteins. Synthetic antibody libraries have proven immensely useful for the de novo isolation of antibodies without the need for animal immunization. Focused libraries designed to recognize particular classes of ligands, such as haptens or proteins, have been employed to facilitate the selection of high affinity antibodies. Focused libraries are built using V regions encoding combinations of canonical structures that resemble the structural features of antibodies that bind the desired class of ligands and sequence diversity is introduced at residues typically involved in recognition. Synthetic antibodies are generated and experimentally validated with different scFv libraries that efficiently generate binders to peptides, a class of molecules that has proven to be a difficult target for antibody generation. Diversity was introduced in the $V_H$ using the profile of amino acids found at positions that frequently contact peptide antigens. Both libraries yielded binders to two model peptides, angiotensin and neuropeptide Y, following screening by solution phage panning In particular, mouse libraries yielded antibodies with high affinities (e.g., below 20 nM) to both targets even though only the $V_H$ had been subjected to diversification.

In some embodiments, nucleic acids capable of binding to specific labels are attached to the natural or synthetic antibodies to generate the signals that ultimately create the molecular barcodes and/or indicia. In some embodiments, one or more secondary antibodies are used to generate the signals.

In some embodiments, synthetically evolved small peptides are used as "synthetic antibodies." The peptides have nanomolar affinity to target proteins and can be around 10 amino acids or longer; around 12 amino acids or longer; around 15 amino acids or longer; around 18 amino acids or longer; around 20 amino acids or longer; around 22 amino acids or longer; around 25 amino acids or longer; around 30 amino acids or longer; around 35 amino acids or longer; around 40 amino acids or longer; around 50 amino acids or longer; around 60 amino acids or longer; around 80 amino acids or longer; around 100 amino acids or longer; around 120 amino acids or longer; around 150 amino acids or longer; around 180 amino acids or longer; around 200 amino acids or longer; around 250 amino acids or longer; around 300 amino acids or longer around 400 amino acids or longer; or around 500 amino acids or longer.

More details on synthetic antibodies applicable to the present methods and systems can be found, for example, in Cobaugh et al., 2008, "Synthetic Antibody Libraries Focused Towards Peptide Ligands," *J Mol. Biol.* 378(3): 622-633; Benhar I. 2007, "Design of synthetic antibody libraries," *Expert Opin Biol Ther.* 7(5):763-779; Nahary and Benhar, 2009, "Design of a human synthetic combinatorial library of single-chain antibodies," *Methods Mol. Biol.* 525:61-80; Bostrom and Fuh, 2009, "Design and construction of synthetic phage-displayed Fab libraries," *Methods Mol. Biol.* 562:17-35; Fellouse et al., 2004, "Synthetic antibodies from a four-amino-acid code: A dominant role for tyrosine in antigen recognition," *Proc. Natl. Acad. Sci. U.S.A.* 101(34):12467-12472; Agnew et al., 2009, "Iterative in situ click chemistry creates antibody-like protein-capture agents," *Angew Chem Int Ed Eng/*0.48 (27):4944-4948; Rohde et al., 2006, "A non-oxidative approach toward chemically and electrochemically functionalizing Si(111)," *J Am Chem. Soc.* 128(29):9518-9525; each of which (including Supplemental Material) is hereby incorporated by reference herein in its entirety.

In some embodiments, aptamers can be used as probes to bind to cellular constituents, especially proteins. Aptamers are oligonucleic acid or peptide molecules that bind to a specific target molecule. Aptamers are usually created by selecting them from a large random sequence pool, but natural aptamers also exist in riboswitches. More specifically, aptamers can be classified as: DNA or RNA aptamers, which comprise (usually short) strands of oligonucleotides and peptide aptamers, which comprise a short variable peptide domain, attached at both ends to a protein scaffold.

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications.

Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range).

The variable loop length is typically composed of ten to twenty amino acids, and the scaffold may be any protein which has good solubility and compacity properties. Currently, the bacterial protein Thioredoxin-A is the most used scaffold protein, the variable loop being inserted within the reducing active site, which is a -Cys-Gly-Pro-Cys- loop in the wild protein, the two Cysteines lateral chains being able to form a disulfide bridge. Peptide aptamer selection can be made using different systems, but the most used is currently the yeast two-hybrid system. Selection of Ligand Regulated Peptide Aptamers (LiRPAs) has been demonstrated. By displaying 7 amino acid peptides from a novel scaffold protein based on the trimeric FKBP-rapamycin-FRB structure, interaction between the randomized peptide and target molecule can be controlled by the small molecule Rapamycin or non-immunosuppressive analogs.

In some embodiments, AptaBiD or Aptamer-Facilitated Biomarker Discovery is adopted for probe design. AptaBiD is based on multi-round generation of an aptamer or a pool of aptamers for differential molecular targets on the cells which facilitates exponential detection of biomarkers. It involves three major stages: (i) differential multi-round selection of aptamers for biomarker of target cells; (ii) aptamer-based isolation of biomarkers from target cells; and (iii) mass spectrometry identification of biomarkers. The important feature of the AptaBiD technology is that it produces synthetic affinity probes (aptamers) simultaneously with biomarker discovery. In AptaBiD, aptamers are developed for cell surface biomarkers in their native state and conformation. In addition to facilitating biomarker identification, such aptamers can be directly used for cell isolation, cell visualization, and tracking cells in vivo. They can also be used to modulate activities of cell receptors and deliver different agents (e.g., siRNA and drugs) into the cells.

In some embodiments, the aptamer probes themselves comprise labels that can generate signals that create the molecular barcodes or indicia. In some embodiments, secondary or even tertiary labels are used to generate signals that create the molecular barcodes or indicia.

Additional information on aptamer can be found, for example, in Ellington, et al., 1990, "In vitro selection of RNA molecules that bind specific ligands," Nature 346 (6287): 818-822; Bock, et al., 1992, "Selection of single-stranded DNA molecules that bind and inhibit human thrombin," *Nature* 355 (6360): 564-566; Hoppe-Seyler, et al., 2000, "Peptide aptamers: powerful new tools for molecular medicine," *J Mol. Med.* 78 (8): 426-430; Carothers, et al., 2004, "Informational complexity and functional activity of RNA structures," *J Am Chem. Soc.* 126 (16): 5130-5137; Cohen et al., 1998, "An artificial cell-cycle inhibitor isolated from a combinatorial library," *Proc Natl Acad Sci USA.* 95 (24): 14272-14277; Binkowski et al., 2005,"Ligand-regulated peptides: a general approach for modulating protein-peptide interactions with small molecules," *Chem. Biol.* 12(7):847-855; Sullenger et al., 2002, "Emerging clinical applications of RNA," *Nature* 418 (6894): 252-258; Ng E W et al., 2006, "Pegaptanib, a targeted anti-VEGF aptamer for ocular vascular disease," *Nat Rev Drug Discov* 5 (2): 123-132; Drabovich et al., 2006, "Selection of smart aptamers by methods of kinetic capillary electrophoresis," *Anal Chem.* 78 (9): 3171-3178; Cho et al., 2009, "Applications of Aptamers as Sensors," *Annual Review of Analytical Chemistry* 2(1): 241-264; each of which (including Supplemental Material) is hereby incorporated by reference herein in its entirety.

The complexity of a particular barcode or a particular set of barcodes is determined by the ultimate purpose for which the barcodes are intended. For example, if the barcodes are used for profiling of large number of cellular constituents, the barcodes will be more sophisticated. For example, there will be more colors within each respective barcodes. The barcodes will comprise larger number of labeled probes. In addition, there will be more variations in linear frequencies and/or spatial arrangement of the labeled probes with respect to each barcode for large scale profiling type analysis. Alternatively, if the barcodes are intended for quantifying one or more particular cellular constituents or analyzing the interactions between specific cellular constituents, care will be taken to ensure accuracy by using redundant probes and multiplicity in barcoding. For example, probes bound to the same or overlapping region of a particular mRNA transcript can be tagged with different types of labels to provide redundancy data to improve accuracy and precision.

In some embodiments, the same cellular constituent can be represented by multiple barcodes. In some embodiments, only selected regions of a cellular constituent is used in creating a barcode. In some embodiments, the entire cellular constituent is used in creating a barcode.

Figure 1F:
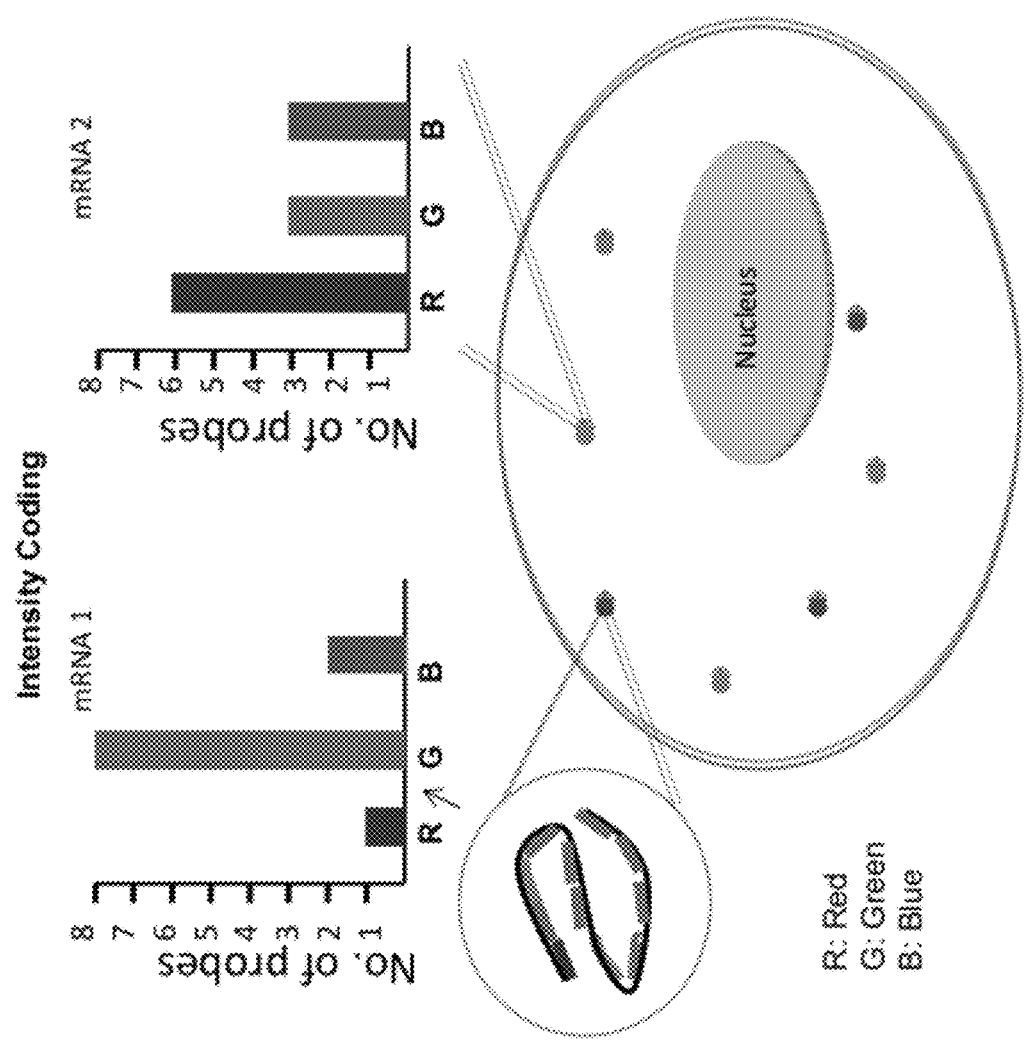

In some embodiments, multiple probes carrying the same type of label are used in creating a barcode/indicium. This design results in differences in intensity of signals observed for different types of signals. FIG. 1F illustrates the concept of intensity barcoding. For example, the molecular barcode of mRNA1 comprises 1 probe associated with a label emitting a red (R) signal; 8 probes associated with a label emitting a green (G) signal; and 2 probes associated with a label emitting a blue (B) signal. The molecular barcode of mRNA2 comprises 6 probe associated with a label emitting a red (R) signal; 3 probes associated with a label emitting a green (G) signal; and 3 probes associated with a label emitting a blue (B) signal. In these embodiments, the intensity of different types of signals (such as light in different color) is observed separately, for example, by different color channel. In some embodiments, redundant coding is needed to correct for hybridization efficiencies.

Figure 1G:
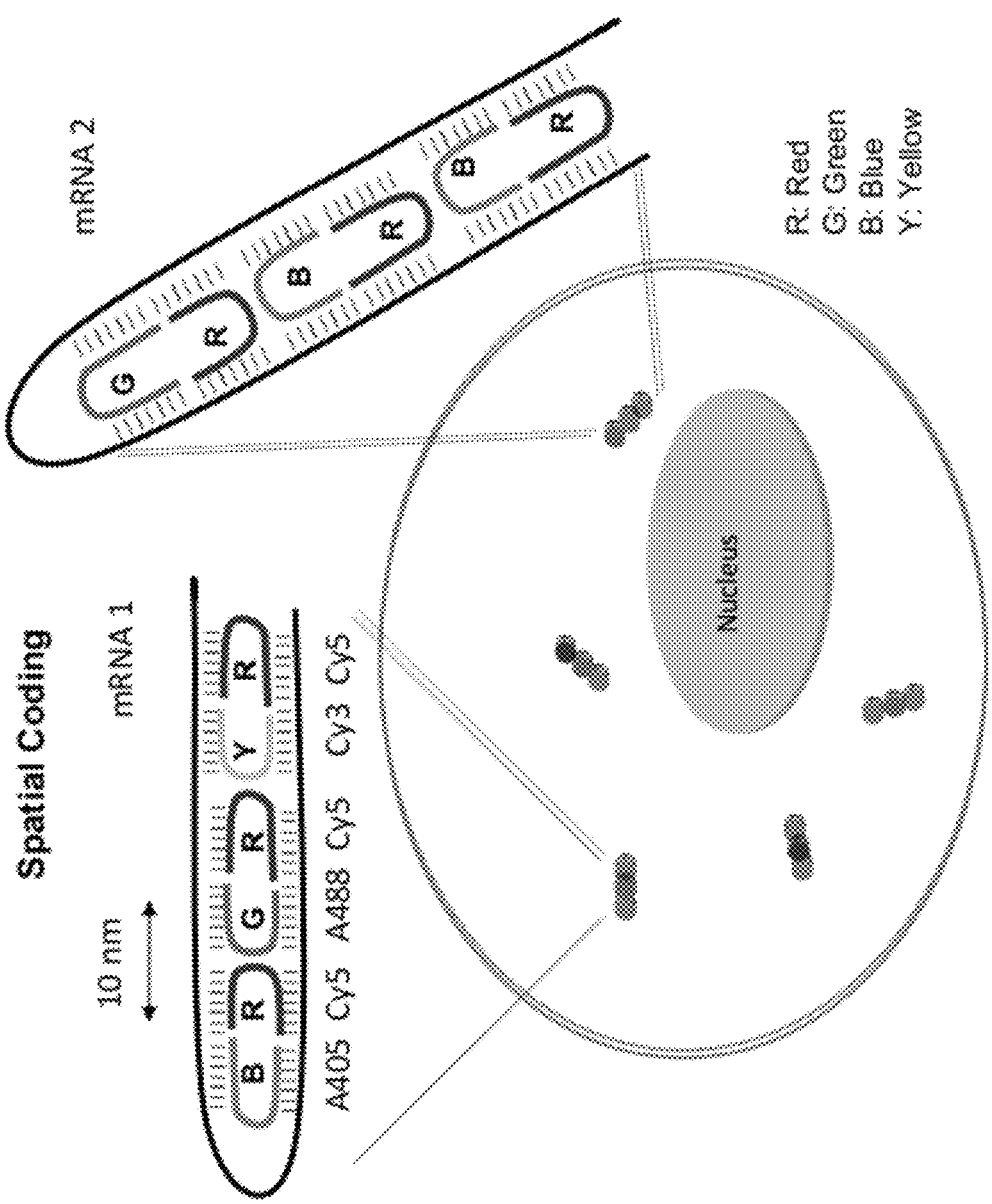

In some embodiments, probes are designed to stable the target cellular constituents, thus increasing the persistence length and stiffening the probe-target cellular constituent complex. The strategy of "spatial barcoding" is depicted in FIG. 1G. For example, mRNA1 and mRNA2 are folded into two closely linked duplex upon binding of the probes. This approach will preserve high coding efficiency and will also allow two dyes in functional STORM dye unit to be brought into close proximity with each other through neighboring oligo probes. This will not only simplify synthesis, but also improve specificity as the only STORM capable probes are the pairs assembled correctly in the stapled structure, reducing background. Alternatively, functionalizing dyes are directly paired on oligo probes, as will be described hereinbelow.

One of skill in the art would understand that, although described in connection with mRNA transcripts, the strategies of intensity barcoding and spatial barcoding are applicable to other cellular constituents.

Additional details on probe design and labeling probes can be found hereinbelow.

Creating Molecular Barcodes/Indicia

As described above, an important aspect in creating a molecular barcode is the selection and creation of the probes that specifically recognize a target cellular constituent. As illustrated above, when the target cellular constituent is an mRNA transcript, the probes that are used to recognize and bind to the mRNA transcript are oligonucleotides, or oligos. In some embodiments, the oligo probes are 10-mer or longer. In some embodiments, the oligo probes are 15-mer or longer. In some embodiments, the oligos are 20-mer or longer; 25-mer or longer; 30-mer or longer; 40-mer or longer; 50-mer or longer; 70-mer or longer; 100-mer or longer; 150-mer or longer; 200-mer or longer; 250-mer or longer; 300-mer or longer; 500-mer or longer; or 1,000-mer or longer.

In some embodiments, the oligo probes are designed by using complementary sequences to randomly selected sequences or segment of sequences in a target cellular constituent (e.g., an mRNA transcript).

In some embodiments, the oligo probes are designed by deliberately selecting sequences or segment of sequences that bind to a target cellular constituent (e.g., an mRNA transcript) with known or predicted binding affinity. This is called "intelligent probe design," where structure, sequence and biochemical data are all considered to create probes that will likely have better binding properties to a target cellular constituent. In particular, the preferred regions in a target cellular constituent are either identified experimentally or predicted by algorithms based on experimental data or computation data. For example, computed binding energy and/or theoretical melting temperature can be used as selection criteria in intelligent probe design.

Tools are available for automated designs of probes that will have either actual or predicted optimal binding properties to the target cellular constituents. For example, the Designer program is routinely used for designing probes that bind to a particular target RNA sequence as part of the established single molecule RNA Fluorescent in-situ hybridization technology (FISH), which was developed at the University of Medicine and Dentistry of New Jersey (UMDNJ) a Single Molecule Fluorescent in-situ hybridization technology based on detection of RNA (singlemoleculefish<dot>com/designer<dot>html). For the Designer program, the open reading frame (ORF) of the gene of interest is typically used as input. This approach is used to exclude the more repetitive regions and low complexity sequence contained in Un-translated Regions (UTRs). Probes are designed to minimize deviations from the specified target GC percentage. The program will output the maximum number of probes possible up to the number specified. Sequence input is stripped of all non-sequence characters. A user can specify parameters such as the number of probes, target GC content, length of oligonucleotide and spacing length. Most success has been achieved with target GC contents of 45%. Typically, oligos are designed as 20 nucleotides in length and are spaced a minimum of two nucleotides apart.

To ensure accuracy, three major design considerations to target coding sequences of gene transcripts are used 1) mRNA length, 2) repeat sequences and 3) sequences of low complexity (such as GC content). As for length, the number of probes that can be accommodated for robust detection is primarily sequence dependent. Naturally longer RNA transcripts would require more probes or longer probes to ensure accuracy. Repetitive elements and low complexity sequences must be screened in advance and manually removed, further restricting the sequence space available for design. For this reason, certain genes such as the keratins may present unusual challenges. The optimal target has an overall GC content of 40-50%, although mRNAs with higher GC content may yield good results by using more stringent washing conditions.

The Stellaris RNA FISH method is applicable to a variety of biological specimens, including but not limited to bacteria, yeast, mammalian cells, *C. elegans* embryos and L1-L2 larvae, *Drosophila melanogaster* wing imaginal discs, and primary rat hippocampal neurons.

Additional description of single molecule FISH can be found in, for example, Raj A., et al., 2008, "Imaging individual mRNA molecules using multiple singly labeled probes," *Nature Methods* 5(10): 877-879; Femino A., et al., 1998, "Visualization of single RNA transcripts in situ," *Science* 280: 585-590; Vargas D., et al., 2005, "Mechanism of mRNA transport in the nucleus," *Proc. Natl. Acad. Sci. of USA* 102: 17008-17013; Raj A., et al., 2006, "Stochastic mRNA synthesis in mammalian cells," *PLoS Biology* 4(10): e309; Maamar H., et al., 2007, "Noise in gene expression determines cell fate in *B. subtilis*," Science, 317: 526-529; and Raj A., et al., 2010 "Variability in gene expression underlies incomplete penetrance," *Nature* 463:913; each of which (including any Supplemental Material) is hereby incorporated by reference herein in its entirety.

The rationale of intelligent probe design also applies to probes that are not nucleic acids such as proteins. Given the three-dimensional nature of protein molecules, intelligent designs of antibody probes that would bind to a target cellular constituent can be more challenging. For example, protein structures and known epitope data or prediction algorithms will be considered to identify accessible surface epitopes that will likely combine to create an indicium or molecular barcode that is associated with the target cellular constituent and can be used to identify it within a cellular environment or to determine properties associated with the target cellular constituent, such as location within the cell and possible binding partners.

In some embodiments, protein indicia can be identified by in vitro analysis. For example, purified protein samples can be conjugated with one or more labeled antibodies. The locations of these antibodies can then be determined by electron microscopy, X-ray diffraction, or combined methods. Electron microscopes (EM) have a greater resolving power than a light-powered optical microscope, because electrons have wavelengths about 100,000 times shorter than visible light (photons), and can achieve better than 0.2 nm resolution and magnifications of up to 2,000,000×. The pre-determined indicia can then be used as standards (or positive controls) to assist the identification of molecular indicia or barcodes of proteins in a cell using the super resolution technologies of the present invention.

In some embodiments, the present methods and systems can be use to carry out by whole cell labeling of nucleic acids and proteins. Previously, over 1,000 genes were each tagged individually in different cells with fluorescent labels, and then protein and mRNA copies in individual cells were counted using a high-throughput system. In another example, over 7,000 genes were classified by applying FISH to one gene one at a time in the Berkeley fly genome project. See, for example, insitu<dot>fruitfly<dot>org; Taniguchi Y., et al., 2010, "Quantifying *E. coli* proteome and transcriptome with single-molecule sensitivity in single cells," *Science* 329:533-538; Tomancak et al., 2002, "Systematic determination of patterns of gene expression during *Drosophila embryogenesis,*" *Genome Biol.* 3(12):1-14; Tomancak et al., 2007, "Global analysis of patterns of gene expression during *Drosophila embryogenesis*," Genome Biol. 8(7): R145; each of which (including any Supplemental Material) is hereby incorporated by reference herein in its entirety. By using different molecular barcodes, the present systems and methods all allow one to label multiple cellular constituents in the same cell.

It will be understood by one of skill in the art that indicia corresponding to longer, larger or more complex cellular constituents require more sophisticated combination of probes. For example, probes of longer oligonucleotides or more probes are needed to recognize and distinguish mRNA transcripts bearing similar sequences. Similarly, distinguishing proteins bearing similar structural or functional domains will also require more complex indicia.

It will be understood by one of skill in the art that the current methods and systems can be applied to a combination of cellular constituents. For example, DNA, RNA and protein can be labeled and analyzed in one single experiment.

One of skill in the art would also understand that length or size of probes will vary, depending on the target cellular constituents and purposes of the analysis.

Labels are associated with the specific probes to allow them to emit signals that will be used in subsequence super resolution analysis. Any labels suitable for generating such signals can be used in the present invention. In some embodiments, the signals are generated by fluorophores. Fluorescent labeling, e.g., the process of covalently attaching a fluorophore to a probe that binds to a cellular constituent (such as a protein or nucleic acid). This is generally accomplished using a reactive derivative of the fluorophore that selectively binds to a functional group contained in the target molecule. In some embodiments, exemplary probes to which the labels are attached include but are not limited to antibodies, proteins, amino acids and peptides. Fluorescent labeling is accomplished using a chemically reactive derivative of a fluorophore. Common reactive groups include amine reactive isothiocyanate derivatives such as FITC and TRITC (derivatives of fluorescein and rhodamine), amine reactive succinimidyl esters such as NHS-fluorescein, and sulfhydryl reactive maleimide activated fluors such as fluorescein-5-maleimide. Reaction of any of these reactive dyes with another molecule results in a stable covalent bond formed between a fluorophore and a labeled molecule.

Following a fluorescent labeling reaction, it is often necessary to remove any non-reacted fluorophore from the labeled target molecule. This is often accomplished by size exclusion chromatography, taking advantage of the size difference between fluorophore and labeled protein, nucleic acid, etc. Fluorophores may interact with the separation matrix and reduce the efficiency of separation. For this reason, specialized dye removal columns that account for the hydrophobic properties of fluorescent dyes are sometimes used. Reactive fluorescent dyes are available from many sources. They can be obtained with different reactive groups for attachment to various functional groups within the target molecule. They are also available in labeling kits that contain all the components to carry out a labeling reaction.

In some embodiments, labels of the present invention comprise one or more fluorescent dyes, including but not limited to fluorescein, rhodamine, Alexa Fluors, DyLight fluors, ATTO Dyes, or any analogs or derivatives thereof.

In some embodiments, labels of the present invention include but are not limited to fluorescein and chemical derivatives of fluorescein; Eosin; Carboxyfluorescein; Fluorescein isothiocyanate (FITC); Fluorescein amidite (FAM); Erythrosine; Rose Bengal; fluorescein secreted from the bacterium *Pseudomonas aeruginosa*; Methylene blue; Laser dyes; Rhodamine dyes (e.g., Rhodamine, Rhodamine 6G, Rhodamine B, Rhodamine 123, Auramine O, Sulforhodamine 101, Sulforhodamine B, and Texas Red).

In some embodiments, labels of the present invention include but are not limited to ATTO dyes; Acridine dyes (e.g., Acridine orange, Acridine yellow); Alexa Fluor; 7-Amino actinomycin D; 8-Anilinonaphthalene-1-sulfonate; Auramine-rhodamine stain; Benzanthrone; 5,12-Bis(phenylethynyl)naphthacene; 9,10-Bis(phenylethynyl)anthracene; Blacklight paint; Brainbow; Calcein; Carboxyfluorescein; Carboxyfluorescein diacetate succinimidyl ester; Carboxyfluorescein succinimidyl ester; 1-Chloro-9,10-bis(phenylethynyl)anthracene; 2-Chloro-9,10-bis(phenylethynyl)anthracene; 2-Chloro-9,10-diphenylanthracene; Coumarin; Cyanine dyes (e.g., Cyanine such as Cy3 and Cy5, DiOC6, SYBR Green I); DAPI, Dark quencher, DyLight Fluor, Fluo-4, FluoProbes; Fluorone dyes (e.g., Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin); Fluoro-Jade stain; Fura-2; Fura-2-acetoxymethyl ester; Green fluorescent protein, Hoechst stain, Indian yellow, Indo-1, Lucifer yellow, Luciferin, Merocyanine, Optical brightener, Oxazin dyes (e.g., Cresyl violet, Nile blue, Nile red); Perylene; Phenanthridine dyes (Ethidium bromide and Propidium iodide); Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate)ruthenium(II), Texas Red, TSQ, Umbelliferone, or Yellow fluorescent protein.

In some embodiments, labels of the present invention include but are not limited to Alexa Fluor family of fluorescent dyes (Molecular Probes, Oregon). Alexa Fluor dyes are typically used as cell and tissue labels in fluorescence microscopy and cell biology. The excitation and emission spectra of the Alexa Fluor series cover the visible spectrum and extend into the infrared. The individual members of the family are numbered according roughly to their excitation maxima (in nm). Alexa Fluor dyes are synthesized through sulfonation of coumarin, rhodamine, xanthene (such as fluorescein), and cyanine dyes. Sulfonation makes Alexa Fluor dyes negatively charged and hydrophilic. Alexa Fluor dyes are generally more stable, brighter, and less pH-sensitive than common dyes (e.g. fluorescein, rhodamine) of comparable excitation and emission, and to some extent the newer cyanine series. However, they are also more expensive. Exemplary Alexa Fluor dyes include but are not limited to Alexa-350, Alexa-405, Alexa-430, Alexa-488, Alexa-500, Alexa-514, Alexa-532, Alexa-546, Alexa-555, Alexa-568, Alexa-594, Alexa-610, Alexa-633, Alexa-647, Alexa-660, Alexa-680, Alexa-700, or Alexa-750.

In some embodiments, labels of the present invention comprise one or more rom the DyLight Fluor family of fluorescent dyes (Dyomics and Thermo Fisher Scientific). Exemplary DyLight Fluor family dyes include but are not limited to DyLight-350, DyLight-405, DyLight-488, DyLight-549, DyLight-594, DyLight-633, DyLight-649, DyLight-680, DyLight-750, or DyLight-800.

In some embodiments, the same type of labels can be attached to different probes for different types of cellular constituents, including nucleic acids and proteins.

For example, in some embodiments, DNA or RNA probes are labeled with either Cy3 or Cy5 that has been synthesized to carry an N-hydroxysuccinimidyl ester (NHS-ester) reactive group. Since, NHS-esters react readily only with aliphatic amine groups, which nucleic acids lack, nucleotides have to be modified with aminoallyl groups. This can be done through incorporating aminoallyl-modified nucleotides during synthesis reactions. In some embodiments, a label is used in every 60 bases to avoid quenching effects.

For example, in some embodiments, protein probes (e.g., antibodies) are also labeled with either Cy3 or Cy5. For protein labeling, Cy3 and Cy5 dyes sometimes bear maleimide reactive groups instead. The maleimide functionality allows conjugation of the fluorescent dye to the sulfhydryl group of cysteine residues. Cysteines can be added and removed from the protein domain of interest via PCR mutagenesis. Cy5 is sensitive to the electronic environment in which it resides. Changes in the conformation of the protein to which the label is attached can produce an enhancement or quenching of the emission. The rate of this change can be measured to determine enzyme kinetic parameters. Cy3 and Cy5 are used in proteomics experiments so that samples from two sources can be mixed and run together thorough the separation process. This eliminates variations due to differing experimental conditions that are inevitable if the samples were run separately. These variations make it extremely difficult, if not impossible, to use computers to automate the acquisition of the data after the separation is complete. Using these dyes makes the automation trivial.

One of skill in the art would understand that choices for a label are determined based on a variety of factors, including, for example, size, types of signals generated, manners attached to or incorporated into a probe, properties of the cellular constituents including their locations within the cell, properties of the cells, types of interactions being analyzed, and etc.

Incorporating Labels into Probes

In some embodiments, labels such as fluorophores are attached to the probes as a secondary addition. In these embodiments, the probes are synthesized or formed prior to the addition of the labels. In some embodiments, labels such as fluorophores are attached to specific locale of the probes. For example, pre-synthesized probes (e.g., oligonucleotides or peptides) are mixed with fluorophores under predefined reaction conditions such that result in attachment of the fluorophores to the probes.

In some embodiments, labels are embedded within the probes themselves. In these embodiments, one or more labels are incorporated into probes while they are being synthesized or formed. For example, a fluorophore can be embedded in an oligonucleotide probe during synthesis. In some embodiments, one or more labels (e.g., fluorophores) are attached to multiple identical probes (e.g., oligos with identical sequences).

In some embodiments, different labels (e.g., fluorophores) are attached to multiple identical probes (e.g., oligos with identical sequences). For example, multiple indicia can be created with minor variations in signal arrangement for the same cellular constituent. Such near-redundancy or near-duplicity is used to ensure accuracy of barcoding. In some embodiments, the same label (e.g., fluorophores emitting red light at the same wavelength) is attached to multiple identical probes (e.g., oligos with identical sequences).

In some embodiments, for example, when aptmers are used as probes, signal-emitting labels are added in a secondary or tertiary step. For example, aptmers specifically bind to a protein are first synthesized. Complementary DNA oligos, which already have labels attached or embedded, are added later to allow binding to the DNA element in the aptmers. In such embodiments, signal-emitting labels are not directly associated with the probes, but through an intermediary composition—the DNA molecule in an aptmer. Similarly, intermediary binding partners of peptide element or RNA element of an aptmer can also be used to affixing labels that will emit the signals for the molecular barcodes or indicia.

Here, an intermediary composition is any molecule or structure to which a label can be attached or embedded to form the final molecular barcodes or indicia. Exemplary intermediary compositions include but are not limited to a DNA or derivatives thereof, an RNAs or derivatives thereof, a DNA-RNA hybrids or thereof, a peptide or analogs thereof, In some embodiments, multiple intermediary compositions can be used to permit final attachment of labels that emit the signals for the molecular barcodes or indicia. For example, the number of intermediary composition used can be one, two, three, four, five, six, seven or more, or ten or more.

In some embodiments, when fluorophores are used as labels, a spare, optically resolvable subset of fluorophores is selectively activated by using photo-switchable fluorophores. For example, multicolor super resolution imaging can be done with a family of photo-switchable fluorescent probes, using Stochastic Optical Reconstruction Microscopy (STORM). Some of the commonly used fluorophores, such as Cyanine dyes can undergo reversible photoswitching, where the fluorophore can be switched between a fluorescent state and a dark state upon illumination at different wavelengths. The rate of switching to the dark state depends on the concentration of the primary thiol in the solution and the solution pH in a manner quantitatively consistent with the formation of an encounter complex between the cyanine dye and ionized thiol prior to their conjugation. Mass spectrometry suggests that the photo-conversion product is a thiol—cyanine adduct in which covalent attachment of the thiol to the polymethine bridge disrupts the original conjugated π-electron system of the dye. In particular, Cy5 has demonstrated such "optical switching" properties: its fluorescence emission can be switched on and off using pulses of light. During each excitation, Cy5 emits thousands of photons before going dark. A brief pulse of ultraviolet light will then efficiently reactivate the molecule to its fluorescent state, and this process can be repeated for hundreds of cycles. The switchable fluorescence exhibited by Cy5 is a strongly nonlinear process, and this nonlinearity could be used to overcome the diffraction limit of resolution.

In some embodiments, a probe is associated with a photo-switchable "reporter" fluorophore that can be cycled between fluorescent and dark states, and an "activator" that facilitates photo-activation of the reporter. In some embodiments, pairs of reporter-activator fluorophores are used as labels. Combinatorial pairing of reporters and activators allows the creation of probes with many distinct colors. Iterative, color-specific activation of sparse subsets of these probes allows their localization with nanometer accuracy, enabling the construction of a super-resolution STORM image. Using this approach, multicolor imaging of DNA model samples and mammalian cells can be done with 20- to 30-nanometer resolution.

In some embodiments, photo-switchable "reporter" fluorophore are used in the context of protein. When Cy5 is paired with a second fluorophore (such as Cy2 or Cy3), its activation wavelength is strongly influenced by the spectral characteristics of its neighbor. Hence, selectively activating specific populations of dye pairs has allowed the capture of images of multiple molecular targets within the same sample. With antibodies labeled with either Cy3 and Cy5, or Cy2 and Cy5, microtubules and clathrin-coated pits in cultured mammalian cells have been imaged.

In some embodiments, pools of probes are use against multiple target cellular constituents using a tiered strategy (Table 1 and FIGS. 4A-4D), similar to that described in Huffman coding. For example, more strongly expressed genes are coded with least complex barcodes, while less strongly expressed genes are coded with more complex barcodes.

Figure 3:
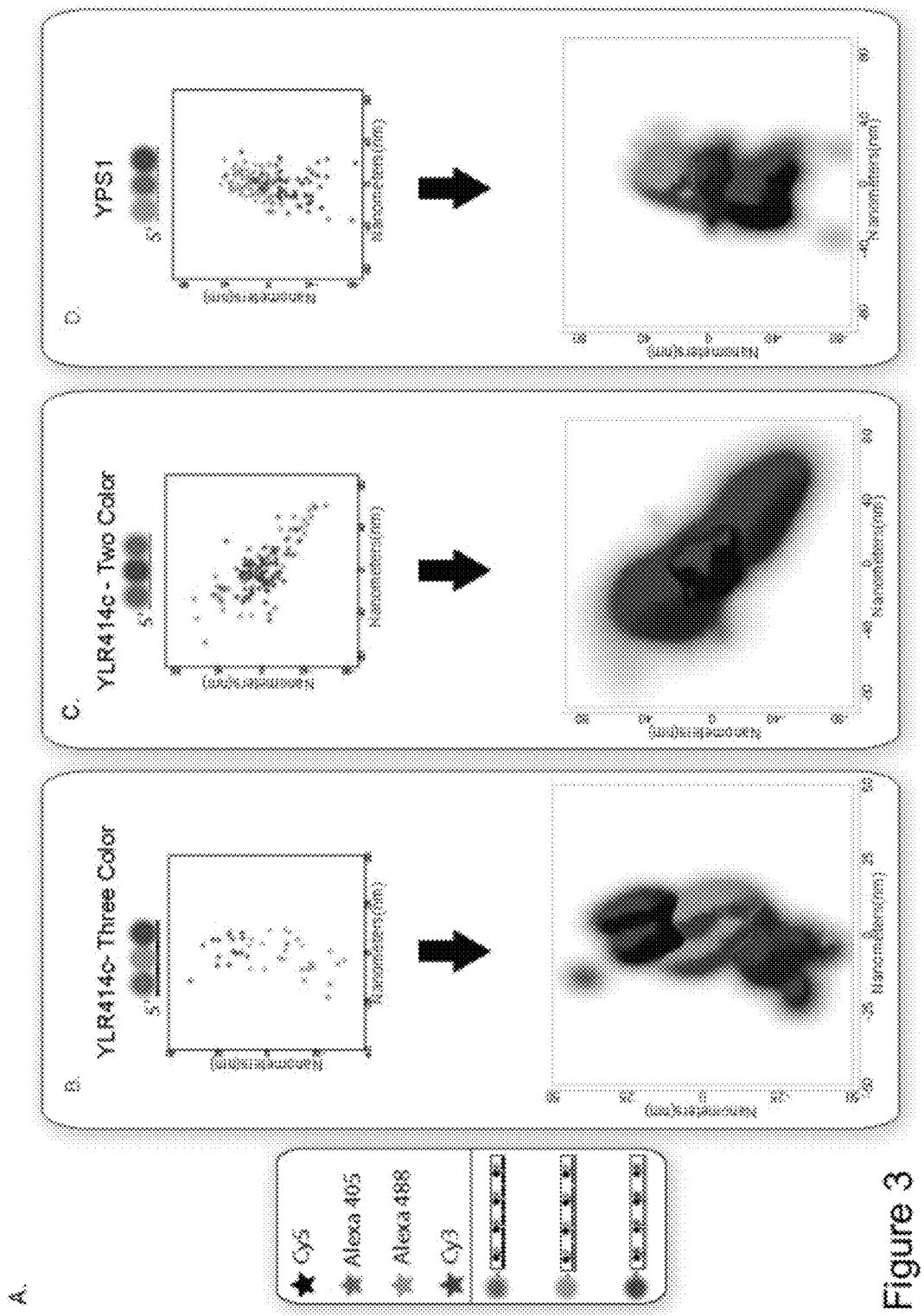
FIGS. 3A-3D depict exemplary embodiments, demonstrating spatial order on transcripts resolved by Stochastical Optical Reconstruction Microscopy (STORM). A. Each color of the barcode consists of 4 pairs of fluorophores grouped together on pairs of probes with an activator at the 5' adjacent to a 3' Cy5. Barcode resolution is independent of transcript identity. B). 3 color barcodes on YLR414c transcript. C) A repeat 2 color barcode on the YLR414c mRNA. Note the localizations of two identical but spatially separated colors. Repeat coding in principle allows infinite combinations of barcodes. D) 3 color barcode on YPS1 mRNA. The order of the probes is represented by the cartoon. A histogram of the STORM reconstruction of a single barcode is shown along with the raw localization activation scatterplots.

Additional details concerning photo-switchable fluorophores used as labels can be found in connection with disclosure concerning FIG. 3.

More details on switchable fluorophores can be found, for example, in Bates et al., 2007, "Multicolor Super-Resolution Imaging with Photo-Switchable Fluorescent Probes," *Science* 317(5845): 1749-1753 and Supplemental Online Material, and Dempsey et al., 2009, "Photoswitching Mechanism of Cyanine Dyes," *J. Am. Chem. Soc.*, 131(51): 18192-18193, each of which (including any Supplemental Material) is hereby incorporated by reference herein in its entirety.

Hybridization of Probes to Target Cellular Constituents

Labeled probes are subsequently introduced into the cell and hybridized to target cellular constituents. In general, in situ hybridization of yeast cells is almost identical to mammalian cells, except that the cell wall has to be removed by spheroplasting the yeast cells prior to hybridization. Additional details can be found, for example, in Long R M, et al., 1995, *RNA* (10): 1787-1794 and at singlemoleculefish<dot>com/protocols<dot>html, each of which (including any Supplemental Material) is hereby incorporated by reference herein in its entirety.

In some embodiments, a hybridization process comprises the steps of probe preparation, fixation, hybridization, washing, and mounting. In some embodiments, RNAse treatment and antibody detection are also included.

One of skill in the art would understand that hybridization conditions of the probes to target cellular constituents change with respect to the specific purposes for which a barcoding method/system is used.

Resolving Barcodes or Indicia—De-coding the Barcodes

In some embodiments, signals from cellular constituents bearing multi-signal molecular barcodes are recorded at the same time. In some embodiments, signals from cellular constituents bearing multi-signal molecular barcodes are recorded at different times, one signal at a time. Data collected from multiple channels are combined to produce one or more composite images. Cross-talks among labels can be reduced by modifying the probe design, types of label attached, use of equipment with better resolution, or by improving the methods or algorithms by which the data are processed.

In some embodiments, drifts in multichannel experiments are corrected by using fluorescent beads as fiducial markers. These beads can be localized to 1-2 nm using Gaussian fitting, and can be used accurately to correct for small changes in stage positions. In some embodiments, where multi-imaging channels are used, gold nanoparticles can be used to correct for chromatic aberrations. In some embodiments, some magnetic beads are used to correct drifting in multichannel experiments. Additional details on such technologies can be found, for example, in Shroff et al., 2007, "Dual-color superresolution imaging of genetically expressed probes within individual adhesion complexes," *Proc. Natl. Acad. Sci. USA* 104(51):20308-20313 and Bates et al., 2007, "Multicolor Super-Resolution Imaging with Photo-Switchable Fluorescent Probes," Science 317(5845): 1749-1753, which (including any Supplemental Material) is incorporated by reference herein in its entirety.

In some embodiments, Cy5.5 or Cy7 based dyes are used to increase the available color to at least 6. Incorporating Spiroamides can add additional colors to the palette, allowing drastically enhanced multiplex capabilities. Introduction of these dyes would require chromatic corrections on the STORM reconstructed images. In addition, two color repeat barcodes can be used, depending mainly on the photophysical properties of the Cy5 based STORM dyes. The relatively poor contrast ratio (1:200) of the Cy5 based dyes means that stronger than ideal activation power is needed to overcome the non-specific blinking rate of Cy5. This increases the frequency of multiple activation of fluorophores within the same diffraction limited volume, and generates spatial blurring in between the repeat coding position. Thus for the repeat barcode experiments, the activation power is tuned to be above the non-specific activation rate, but lower than the rate that would generate multiple activations within the same diffraction limited spot. Spiroamides and Spirolactones suffer from the similar low contrast ratios. Development of higher contrast ratio fluorophores is thus essential for increasing the multiplex capabilities of the barcoding approach.

In some embodiments, only simple three-color barcodes are implemented where higher activation intensity and multiple switching events in one color do not distort the barcode image to avoid complications caused by the nonspecific blinking of dyes. In some embodiments, the axial dimensions of the fluorophores are resolved. The approach of using astigmatic or dumbbell shaped point-spread-function can improve the axial resolution to 50 nm, which can be helpful to resolve 2 barcoded mRNAs if they overlap in the xy but not z dimension. In some embodiments, interferometric PALM can be used to further resolve axial resolution, e.g., to 5 nm. The ultimate limiting factor in the multiplexing is the contrast ratio of Cy5 dyes. It limits the labeling density as no more than 100 Cy5 molecules can be in the same diffraction limited volume for super-resolution reconstruction and prevents the effective usage of the repeat barcodes.

In some embodiments, techniques are used to achieve z-resolution on super resolution scale, for example, on the nanometer scale. The z-resolution is generally defined as the optical thickness of the optical z-plane. Methods for improving z-resolution are known in the art and can be applied to the present methods and systems.

In some embodiments, as described hereinabove, a Huffman coding type of strategy is used to facilitate signal resolution based on known additional expression data.

In some embodiments, a cell sample is subject to 3D-sectioning to collection data that will be used to reconstruct the three-dimensional structure of the cell. The laser light section method is a 3D-procedure to measure object profiles in one sectional plane. The principle of the laser triangulation requires an orthogonal to the objects surface positioned detector area (e.g., CCD- or CMOS-matrix) to measure the lateral displacement or the deformation of a laser line projected in an angle (between 0 and 90 degrees) onto the objects surface. Laser light sectioning is the two-dimensional extension of the laser triangulation. With projecting the expanded laser line, an elevation profile of the object under test is obtained.

Methods for data processing, especially those for digital imaging data processing can be used in the present invention to improve or optimize the process for resolving barcode/indicium. Digital image processing is the only practical technology for classification, feature extraction, pattern recognition, projection, and multi-scale signal analysis, each of which aspect is applicable to dissolving molecular barcodes/indicia. Exemplary techniques or algorithms that are used in digital image processing include but are not limited to pixelization, linear filtering, principal components analysis, independent component analysis, hidden Markov models, anisotropic diffusion, partial differential equations, self-organizing maps, neural networks, and wavelets.

Indicia created by molecular barcoding are resolved or discerned by super resolution technologies. In some embodiments, super resolution technologies of the present invention include super resolution microscopy. In some embodiments, the super resolution technology has a resolution of about 100 nm or higher; about 80 nm or higher; about 60 nm or higher; about 50 nm or higher; about 40 nm or higher; about 30 nm or higher; about 25 nm or higher; about 20 nm or higher; about 15 nm or higher; about 10 nm or higher; about 8 nm or higher; about 6 nm or higher; about 5 nm or higher; about 4 nm or higher; about 3 nm or higher; about 2 nm or higher; about 1 nm or higher; about 0.5 nm or higher; about 0.2 nm or higher; about 0.1 nm or higher; about 0.05 nm or higher; or about 0.01 nm or higher.

One of skill in the art would understand that the specific characteristics (e.g., size) of the cellular constituents will determine the resolution at which a particular indicium will be resolved.

Super resolution techniques allow the capture of images with a higher resolution than the diffraction limit. They fall into two broad categories, "true" super resolution techniques, which capture information contained in evanescent waves, and "functional" super resolution techniques, which uses clever experimental techniques and known limitations on the matter being imaged to reconstruct a super resolution image. True sub-wavelength imaging techniques include those that utilize the Pendry Superlens and near-field scanning optical microscopy. Most techniques of importance in biological imaging fall into the functional category.

Exemplary super resolution technologies include but are not limited to $I^5M$ and 4Pi-microscopy. Stimulated Emission Depletion microscopy (STEDM), Ground State Depletion microscopy (GSDM), Spatially Structured Illumination microscopy (SSIM), Photo-Activated Localization Microscopy (PALM), Reversible Saturable Optically Linear Fluorescent Transition (RESOLFT), Total Internal Reflection Fluorescence Microscope (TIRFM), Fluorescence-PALM (FPALM), Stochastical Optical Reconstruction Microscopy (STORM), Fluorescence Imaging with One-Nanometer Accuracy (FIONA), and combinations thereof.

Chi, 2009 "Super-resolution microscopy: breaking the limits, Nature Methods 6(1):15-18; Blow 2008, "New ways to see a smaller world," Nature 456:825-828; Hell, et al., 2007, "Far-Field Optical Nanoscopy," Science 316: 1153; R. Heintzmann and G. Ficz, 2006, "Breaking the resolution limit in light microscopy," Briefings in Functional Genomics and Proteomics 5(4):289-301; Garini et al., 2005, "From micro to nano: recent advances in high-resolution microscopy," Current Opinion in Biotechnology 16:3-12; Bewersdorf et al., 2006, "Comparison of $I^5M$ and 4Pi-microscopy," 222(2):105-117; and Wells, 2004, "Man the Nanoscopes," JCB 164(3):337-340; each of which (including Supplemental Material) is hereby incorporated by reference herein in its entirety.

In some embodiments, electron microscopes (EM) are used to resolve an indicium. Electron microscopes have a greater resolving power than a light-powered optical microscope, because electrons have wavelengths about 100,000 times shorter than visible light (photons), and can achieve better than 0.2 nm resolution and magnifications of up to 2,000,000 times.

Exemplary Embodiments of the Methods and Systems

In some embodiments, a plurality of cellular constituents is barcoded by methods and systems of the present invention. For example, molecular barcoding can be applied to one cellular constituent; two or more cellular constituents; three or more cellular constituents; four or more cellular constituents; five or more cellular constituents; six or more cellular constituents; eight or more cellular constituents; ten or more cellular constituents; 15 or more cellular constituents; 20 or more cellular constituents; 30 or more cellular constituents; 50 or more cellular constituents; 80 or more cellular constituents; 100 or more cellular constituents; 150 or more cellular constituents; 200 or more cellular constituents; 300 or more cellular constituents; 500 or more cellular constituents; 1,000 or more cellular constituents; 1,500 or more cellular constituents; or 2,000 or more cellular constituents.

In one aspect, the present invention is used to measure a biological state of a cell, for example, its transcriptional state. The transcriptional state of a cell includes the identities and abundances of the constituent RNA species, especially mRNAs, in the cell under a given set of conditions. For example, a fraction of the constituent RNA species in the cell can be measured for genetic profiling.

In some embodiments, only one type of cellular constituent is analyzed, for example, mRNA transcript. In other embodiments, two or more types of cellular constituents are analyzed. For example, interactions between RNAs and proteins can be analyzed.

In some embodiments, time resolved analysis can be carried out. For example, sample cells can be synchronized by chemical arrest or starvation. Thereafter, cells will be taken at different time points and are sequentially subjected to analysis by molecular barcoding followed by super resolution de-coding. By doing so, a time course of the desired reaction or process can be constructed.

In some embodiments, the present methods and systems can be used to conduct biochemical assay in a single cell setting. For example, the present methods and systems can be used to study interactions between any cellular constituents, including protein-protein interactions, protein-nucleic acid interaction, and etc. In some embodiments, time-resolved biochemical assays can be performed using the present methods and systems.

Additional Embodiments

Transcription Profiling in Single Cells

In some embodiments, a transcriptional state of a cell is imaged by detecting and distinguishing individual mRNAs. Florescence In-Situ Hybridization (FISH) allows single mRNAs molecule in fixed cells to be labeled and imaged. This is accomplished by hybridizing the mRNA with a set of short oligonucleotide probes complementary to the mRNA sequence. Conventionally, these probes are labeled all with the same fluorophore to increase the contrast compared to non-specific bound probes in the cell. This allows individual mRNA to be visualized as a bright fluorescent dot in the cell. In such embodiments, the number of species that can be labeled simultaneously is determined by the availability of spectrally distinct fluorophores. Further, if the expression level of the targeted mRNA is high, then individual hybridized transcripts cannot be optically resolved from each other, preventing accurate quantitation of the copy number.

Figures 2, 7A:
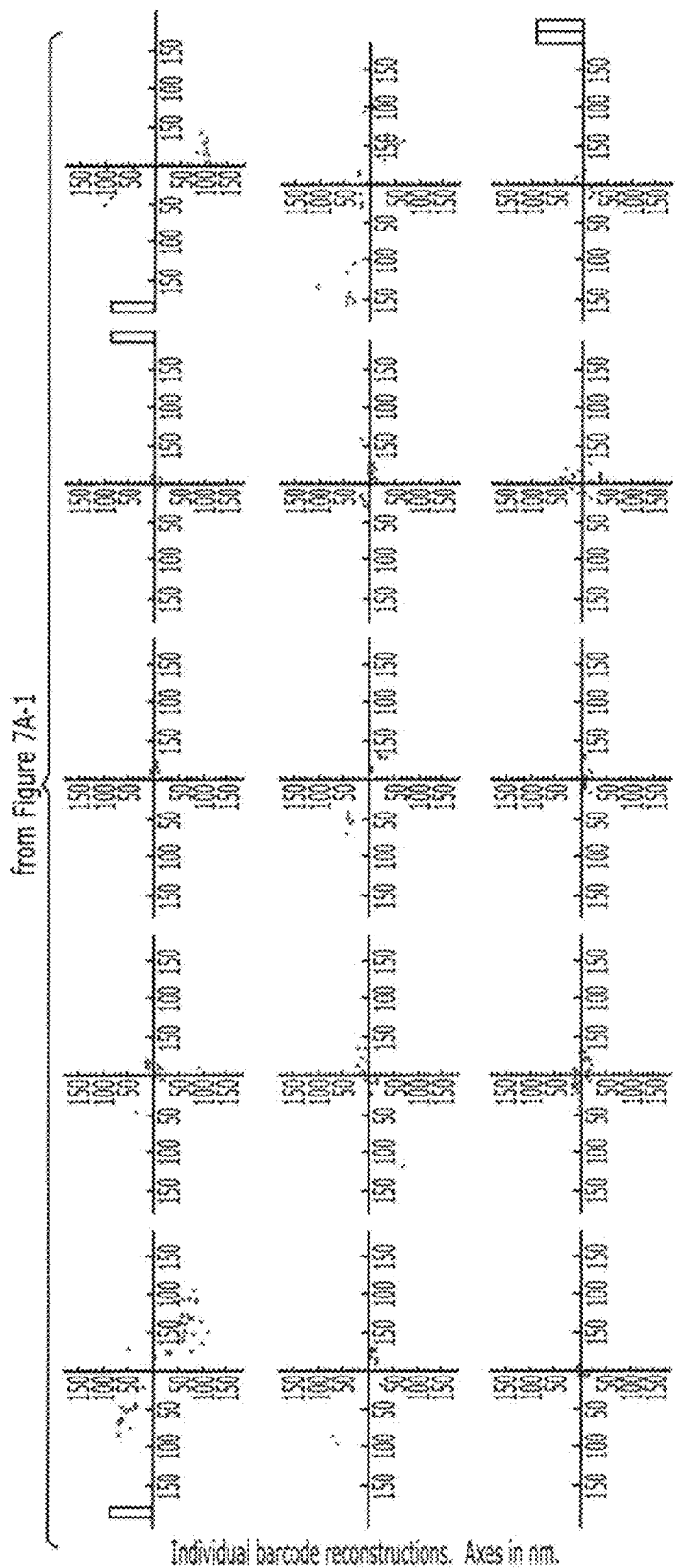
Figures 1, 7B:
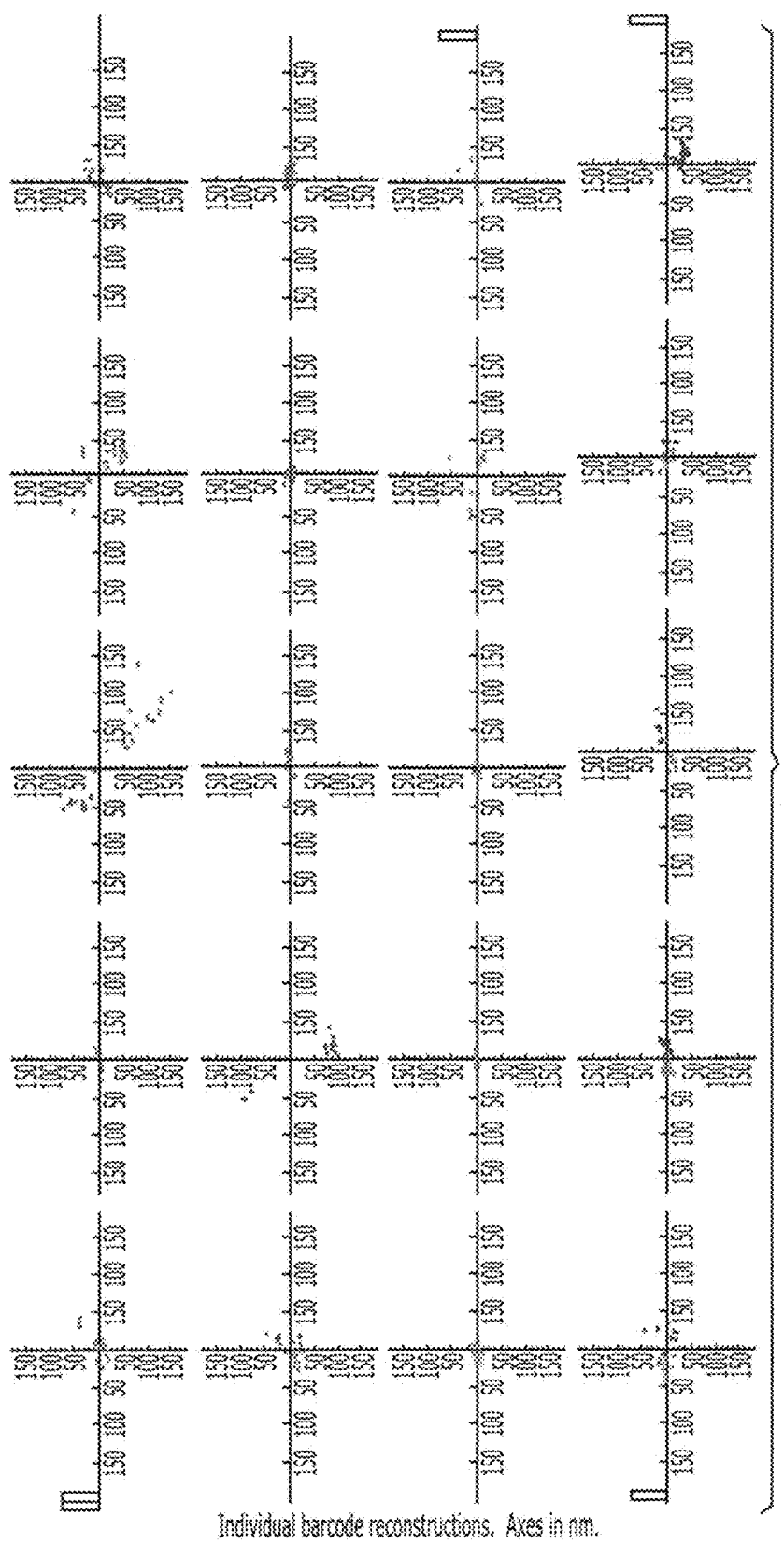
Figures 2, 7B:
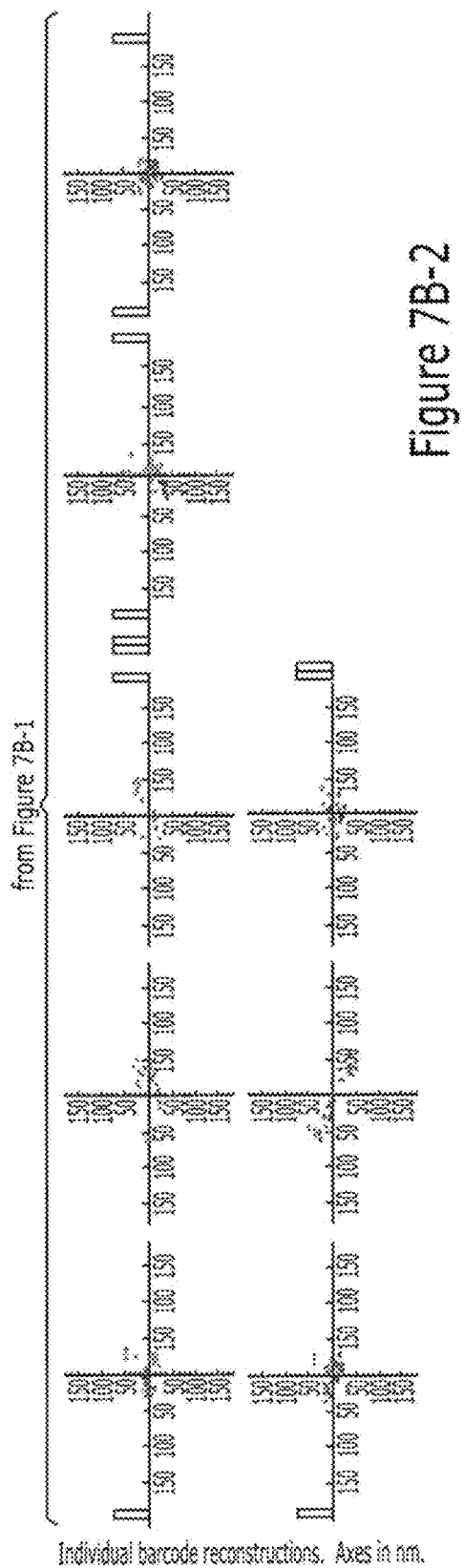
Figure 8A:
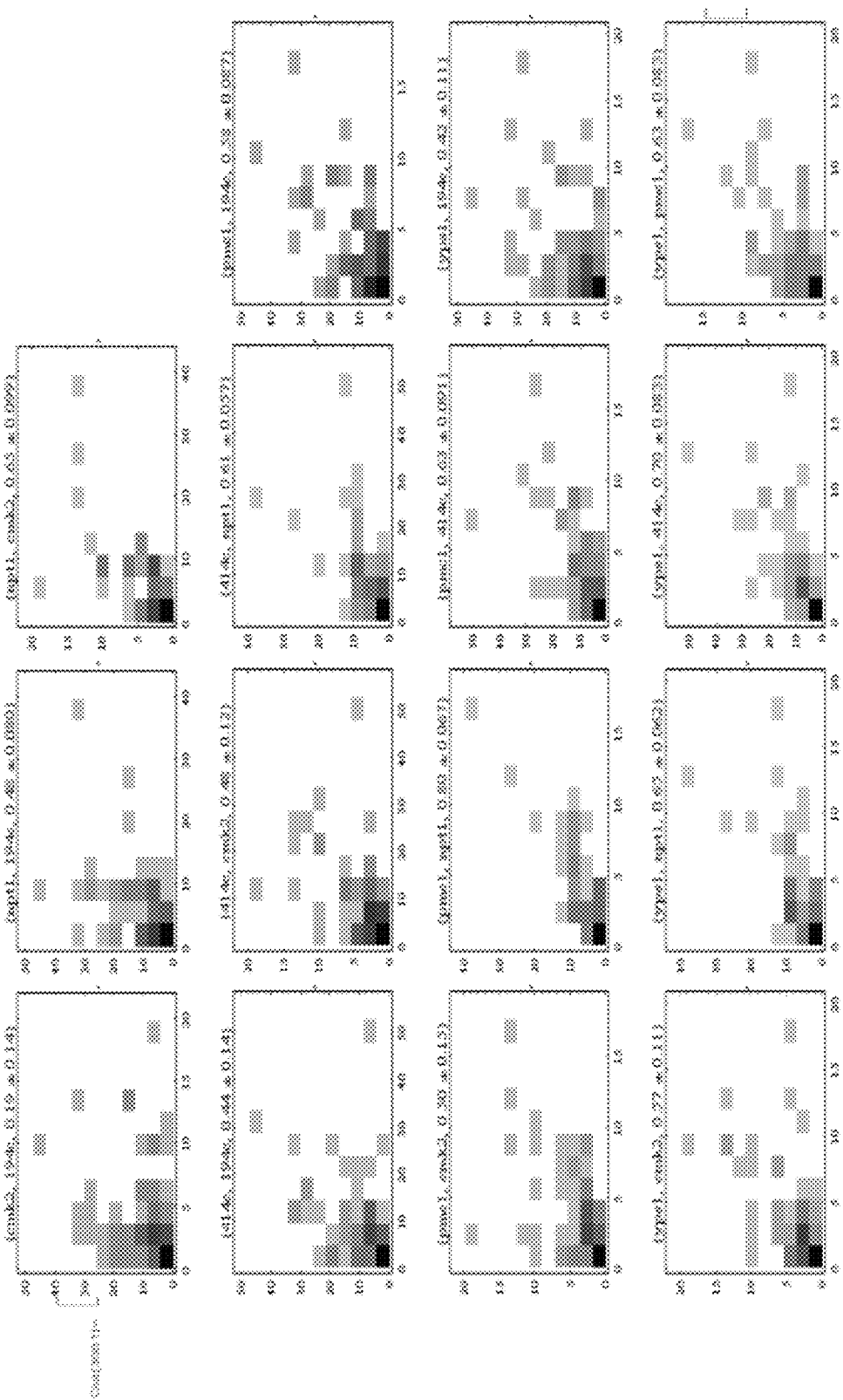
FIGS. 8A and 8B depict exemplary embodiments, showing pairwise correlations in WT (A) and over-expressed Crz1 cells (B). Correlation coefficient and error bar are shown with the gene names.
Figure 8B:
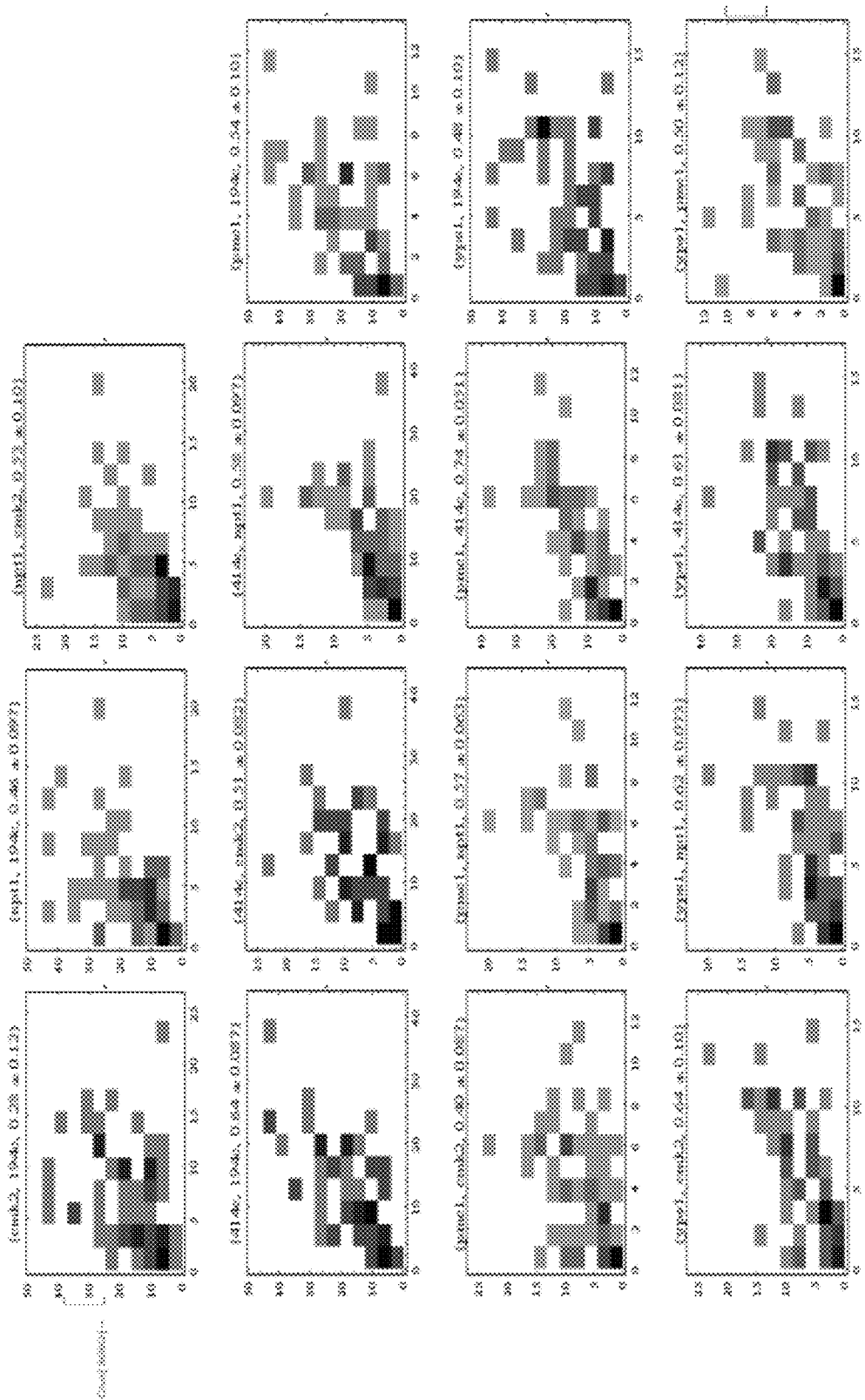

In some embodiments, different super-resolution fluorophores are attached within a set of oligo probes, such that as they hybridize against their target mRNA, a molecular barcode or indicium can be readout by super-resolution microscopy. The barcode can then serve to uniquely identify that particular transcript. Thus, by using different barcodes for different mRNA species, many mRNAs can be labeled simultaneously as illustrated in FIG. 1.

As an example, the current systems have enormous capacity and can effectively barcode the entire human transcriptome with at least 6 distinct super-resolution fluorophores. The entire human transcriptome has about 20,000 genes and 6 distinct super-resolution fluorophores at 6 barcode positions render over 45,000 combinations ($6^6$=46656). In addition, with the giga-pixel volume of a single cell under super-resolution microscopy, individual mRNAs can be imaged and their barcode read out without concerns of overcrowding in the optical space. The expression level for each species of mRNAs can then be tallied by counting the abundance of the corresponding barcodes. This technique not only detects transcripts with single molecule sensitivity, therefore highly accurate in quantitation, but also preserves the intracellular and intercellular spatial context in which transcription occurs. These advantages make it especially applicable for investigations in heterogeneous cell populations, such as cell cultures, tissue sections, and embryos.

Mapping Chromosome Structures

Chromosomal rearrangements have been implicated in many forms of cancer and recent investigations revealed that chromosomes in eukaryotes are packed in a non-linear and complex fashion. Super-resolution barcoding can be applied to image the structure of chromosomes and determine their conformation in single cells. Conventional DNA-FISH can label only 4-5 distinct chromosomal locations limited by the number of distinct fluorophores. However, with the super-resolution barcoding technique, a large set of genomic loci can be labeled each with a distinct barcode and resolved by microscopy. Thus, the physical location of many gene can be mapped and serve as landmarks on the chromosomes, allowing us to detect chromosomal translocations and other rearrangement events in cells. A physical image of the chromosomes in cells with the addresses of individual genes will give us unprecedented look at how the genome is compacted, compare organization in transcriptional active versus repressed regions, and detect subtle changes in genomic structure in tumor cells.

Imaging Transcription Factor Binding in Single Cells.

In some embodiments, the methods and systems described herein are used to analyze transcription factor binding in single cells. Transcription factors (TF) control genes in transcriptional networks through binding sites on the DNA and interactions with regulatory proteins. The distribution of positions and binding states of a particular TF on the chromosome determines the transcriptional program it is accessing in the cell. By fusing TFs with photo-switchable fluorescent protein or labeling with antibodies, the physical location of individual TFs can be determined with 10 nm resolution. The genomic location of the TF can then be assigned by overlaying those positions on top of the high resolution chromosome map developed from technique 2. Results from ChIP-seq experiment will be compared to determine the occupancy of each binding sites and higher order structures at the promoters in single cells. In some embodiments, analysis by the present methods and systems focus specifically on Crz1, a TF in budding yeast that we have shown to pulse in its activity. In some embodiments, the fraction of Crz1 binding sites that are occupied during a pulse will be determined. In some embodiments, it can be determined whether occupancy of different binding sites is correlated depending on their physical proximity in the nucleus. In some embodiments, the extent by which how strongly is TF binding coupled to the transcriptional activity of the promoters.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Probes Design, Purification and Hybridization

Probes (20 mers) were designed to match melting temperature whenever possible with the exception of STORM probes which are designed to be with 2 base pair spacing between the probes to allow efficient reactivation of the STORM pair dyes (FIG. 3A). Labeling and purification of the probes follows the protocol at the smFISH web site (www<dot>singlemoleculefish<dot>com). Yeast cells were grown in minimal media and fixed in log growth phase following the Singer lab protocols, with the minor addition of a 0.1% $NaBH_4$ treatment before ethanol permeabilization step. The $NaBH_4$ treatment significantly decreased the autofluorescence background of the fixed yeast cells. Cells were stored in an eppendorf tubes and aliquot for hybridization experiments. Cells were hybridized with the probes overnight at room temperature in 20% Formamide and 10% dextran sulfate. After hybridization, cells were washed in Formamide and SSC solution 3 times and imaged.

Example 2

Imaging

Imaging of the hybridized cells is carried out on automated fluorescence microscopes. For FIONA, images were acquired on an Olympus IX81 with a 100× sapo objective with laser illumination at 532 nm, 594 nm, and 640 nm. Images were taken with Andor IQ software and an Andor Ikon CCD. FIONA images were acquired in 3 different fluorescence channels (Semrock zero line filters). The centroids of the FISH dots were calculated in each color or wavelength channel and a center of mass of all the dots were calculated and aligned between the channels by a simple translation. This was sufficient for most alignments without additional corrections from rotation and dilations.

STORM imaging was performed on a Nikon Tleclipse microscope with PFS autofocus lock. 640 nm laser (Crystallasers) was used as the main imaging laser and brought to the sample past the critical angle by a TIRFM objective. Lasers at 405 nm, 473 nm and 532 nm were used as activation lasers and automation is controlled by u-manager software. The microscope stages (Prior and ASI) were automated and also controlled by the acquisition software to enable multi-position imaging. Images were then analyzed in a custom written Mathematica script. Buffers used in STORM imaging follows the protocol similar to those in Bates et al., 2007, "Multicolor Super-Resolution Imaging with Photo-Switchable Fluorescent Probes," *Science* 317 (5845): 1749-1753, which (including any Supplemental Material) is incorporated by reference herein in its entirety. Glucose Oxidase was used as the oxygen scavenger and BME was used as the reducing agent.

Example 3

Barcoding Strategy

To multiplex mRNA detection in single cells, 9 target genes of the yeast transcription regulator Crz1 were chosen. A combination of barcodes was used to ensure the accuracy in determining the abundances of each of the genes. To do so, the simplest barcode was designed to the most highly abundant and shortest mRNAs. YLR414c and YLR194c are each 700 bps long and expressed strongly based on microarray experiments. Thus, they were assigned single color barcodes. Cmk2, another highly expressed gene, is also assigned a single color barcode with 12 paired-probes. The next tier expression levels are PMC1, NPT1 and YPS1. These genes were expressed at a lower level and are assigned a 2-position barcode. Lastly, Sok2, GYP7 and PUTT are lowly expressed and are assigned the 3 different 3 color barcodes. As 3 color barcodes were resolved correctly 70% of the times, care was taken to avoid having the incorrectly resolved barcode leaking into other barcodes in significant level. Thus assigning the lowest expressed genes with the most complex barcode mitigate the crosstalk problems.

The barcoding capacity could be drastically improved by using repeat barcodes and more color than the three cy5-pair dyes (FIGS. 3B-3D).

Example 4

Single Cell Profiling and Correlation

The copy number of all of the genes was measured in single cells simultaneously by counting the number of super-resolution reconstructed barcodes (Table 1). Using this data, the distribution of copy numbers for each gene was determined (Figure S) and the pair wise correlation between target genes was calculated. As a control, cells treated with FK506, an inhibitor of the Crz1 pathway, showed negligible expression. This shows that Crz1 pulses are necessary but not sufficient for transcriptional bursts and the stochasticity in promoter initiation can produce uncorrelated bursting in the different targets.

Another question was whether transcription factor availability is limiting in creating stochastic transcription bursting. To do so, the same target genes was profiled in cells with Crz1 strongly expressed from a plasmid (PLE66). The affinity of the promoters to Crz1 can be inferred from the fold change in the expression level of that gene as Crz1 is over-expressed. High affinity promoters such as NPT1 and Pmc1 are expressed at the same levels in wt and over-expressed cells, suggesting the promoter is already saturated at wt Crz1 levels; while lower affinity promoters such as Cmk2 and YLR194c shows a 2 fold increase when Crz1 is over-expressed. There was a stronger correlation between the high affinity promoters likely due to the tight coupling of transcriptional bursting with the Crz1 pulse, whereas in the weaker promoters shows weaker correlation as they burst stochastically and independently following every Crz1 pulse. As Crz1 is over-expressed, the correlation among weak promoters increased, suggesting that promoter occupancy is enhanced. A smaller but non-zero population of cells exhibited bursting in only one gene in over-expressed cells, suggesting that promoter affinity does not explain all of the variations in correlations among genes. In addition, no connection was found between chromosome positions and the gene correlations.

Figures 4A, 4B, 4C, 4D, 4E, 4F, 4G:
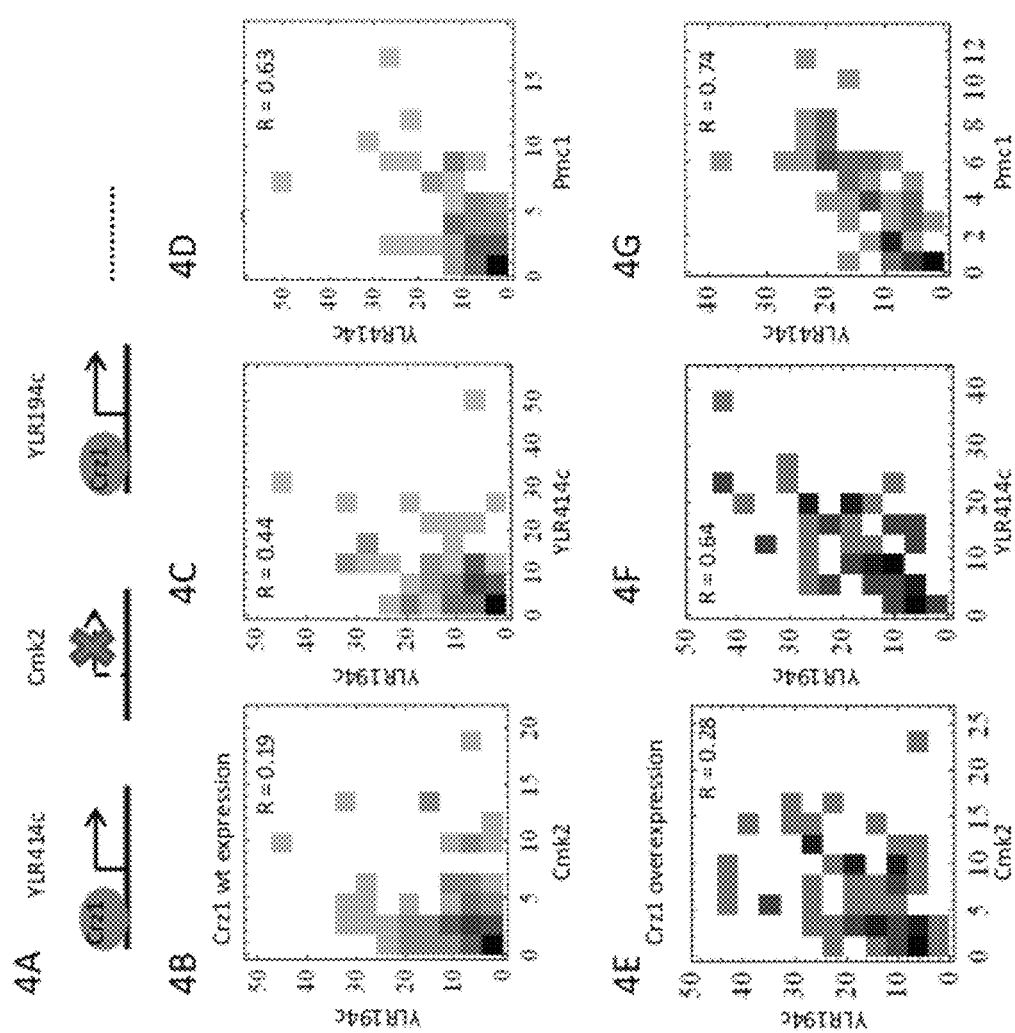
FIGS. 4A-4H depict exemplary embodiments, demonstrating Crz1 target genes respond stochastically to Crz1 pulses. A) Schematic of several promoters responding stochastically to Crz1. B-D) Pairwise correlations between target genes in wt cells. Correlations among promoters with low affinity to Crz1 is weaker than promoters with strong affinity to Crz1, suggesting transcriptional response to Crz1 pulse is stochastic at each promoter and depends on affinity. Promoter strength: Cmk2<194c<414c<Pmc 1. E-G) Correlations in cells with over-expressed Crz1. Significant increase in correlation suggests that Crz1 occupancy controls the stochastic activation of the target promoters. H) A Petrie graph of a 4-dimensional hypercube with each node representing a state with a particular subset of the 4 genes (194c, Cmk2, 414c, Pmc1) strongly expressed. The size of the circle at each node corresponds to the fraction of total cells with that particular expression state. Note that while 194c and 414c are strongly correlated in a pairwise fashion (shown in C), few cells express strongly only 414c and 194c. When both 414c and 194c are expressed strongly, all genes are expressed strongly. The Petrie graph contains higher correlation information not present in the pair-wise correlations.

To elucidate a more global picture of how expressions are correlated, higher order correlations are needed. Each gene was classified as either highly and lowly expressed in a cell, thresholding on the average expression level of that gene in the population, for a total of 29 binary states. The dataset can be mapped to vertices of a 9 dimensional hypercube, which can be collapsed onto a Petrie projection graph (FIG. 4E). The size of the circle at each node of the graph corresponds to the number of cells with a given expression pattern. In a projection of the dataset focusing on 4 genes, we observe that the expressions in most cells are either all high or all low, with a few cells expressing highly in only 1 or 2 of the genes. High affinity and weak promoters behave differently. Two weak promoters were rarely seen on at the same time, because if both of them are on, then the strong promoters are also bound and are expressing. Thus, density is concentrated on singles or triplets or quadruplets. The higher dimensional correlations in the hypercube representation reveal the detailed structures in the regulatory network otherwise lost in the pair-wise correlations.

Example 5 mRNA Extension and Stretching by Compression

Extension of the mRNA to allow spatial resolution of the barcode is essential to the high multiplex potential of the technique. Several approaches were tried to generate spatial extension. First, a DNA origami type of strategy was used to fold the mRNA into a stiff rod like configuration (FIG. 1G). This approach would require each FISH probe to hybridize on two distinct regions of the mRNA. This energy of the hybridization is supposed to fold the mRNA and staple it into a rod. While this approach works with in vitro transcribed mRNA, where an object migrating slower than the native mRNA is seen on the gel, it does not work in mRNAs in fixed cells. We labeled probes such that if the mRNA were successfully folded, then cy3 and cy5 molecules labeled on the probes would be brought together within 1 nm and STORM signal would be observed. While Cy3 and Cy5 hybridization signals are observed, no storm switching and reactivation is observed. This indicates that the probes are bound in one of the positions of the mRNA, but are able to bind to the other site and bring the mRNA into a more compact configuration. Several probe configurations with varying probe length (from 21 mers to 60 mers) were tested with the same results. Second, we applied an electric field to fixed cells in an attempt to generate an electrophoretic effect on the mRNA to lengthen it. Cells were embedded in low melting point agarose and put between 2 electrodes in an electroporation curvette to ensure the E field is applied in a uniform direction. The number of transcripts in the post E-field treated cells were the same as pre E-field treatment and the FIONA reconstructions showed no additional lengthening of the mRNA. These experiments suggest that the mRNA is rigidly held within the fixed cell and are not movable by electromotive forces.

It has been suggested from previous FISH experiments that the mRNA is covalently attached to the protein matrix by formaldehyde. We experimented with fixation methods where only proteins are crosslinked or precipitated to observe the effect on the mRNA. We used the methanol fixation and DSS a NHS ester based protein crosslinker in separate experiments. As methanol fixation is supposed to only precipitate the proteins and do not crosslink nucleic acids, we ask whether we can move the mRNAs out of the cell with an applied E field. Again, the same copy number of transcripts is detected by FISH and the FIONA reconstruction shows no further extension of the mRNA compared to non-electrophoresed cells. This experiment strongly suggest that mRNA is fixed in the cells by interactions of the ribosomes on the mRNA with the protein background during the fixation, rather than through direct nucleic acid to protein interactions. This is consistent with our lack of ability in using DNA origami in folding the mRNA. In a previous experiment, it was suggested short RNAs rapidly escape the cell during the hybridization process and these miRNAs are recovered in the solution [ref]. Our observation of longer transcripts shows that physical escape of the transcript from the cells is improbable and likely hindered by ribosomes, whereas most of the shorter miRNAs most likely do not associate with proteins and thus not permanently fixed in the cell. Experiments with Puromycin and Harringtonine to dissociate or stall the ribosomes were inconclusive probably due to poor permeability and poor kinetics of the compounds at 25-30° C.

Figure 5:
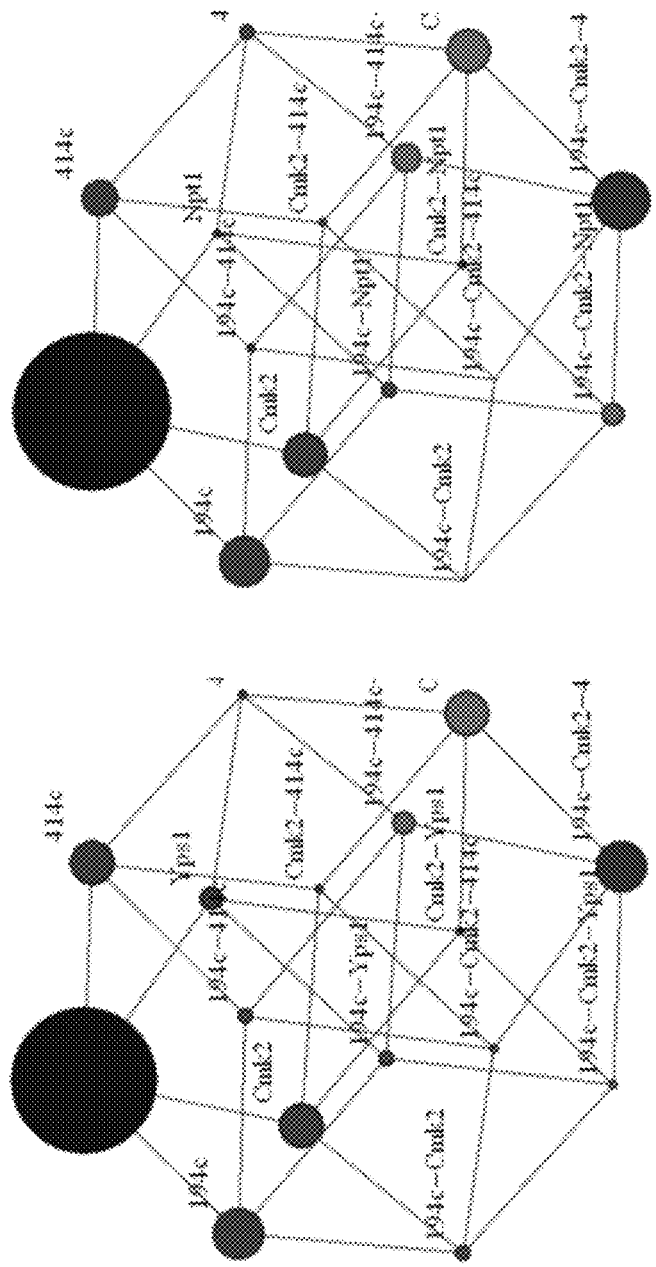
FIG. 5 depicts exemplary embodiments.
Figure 6:
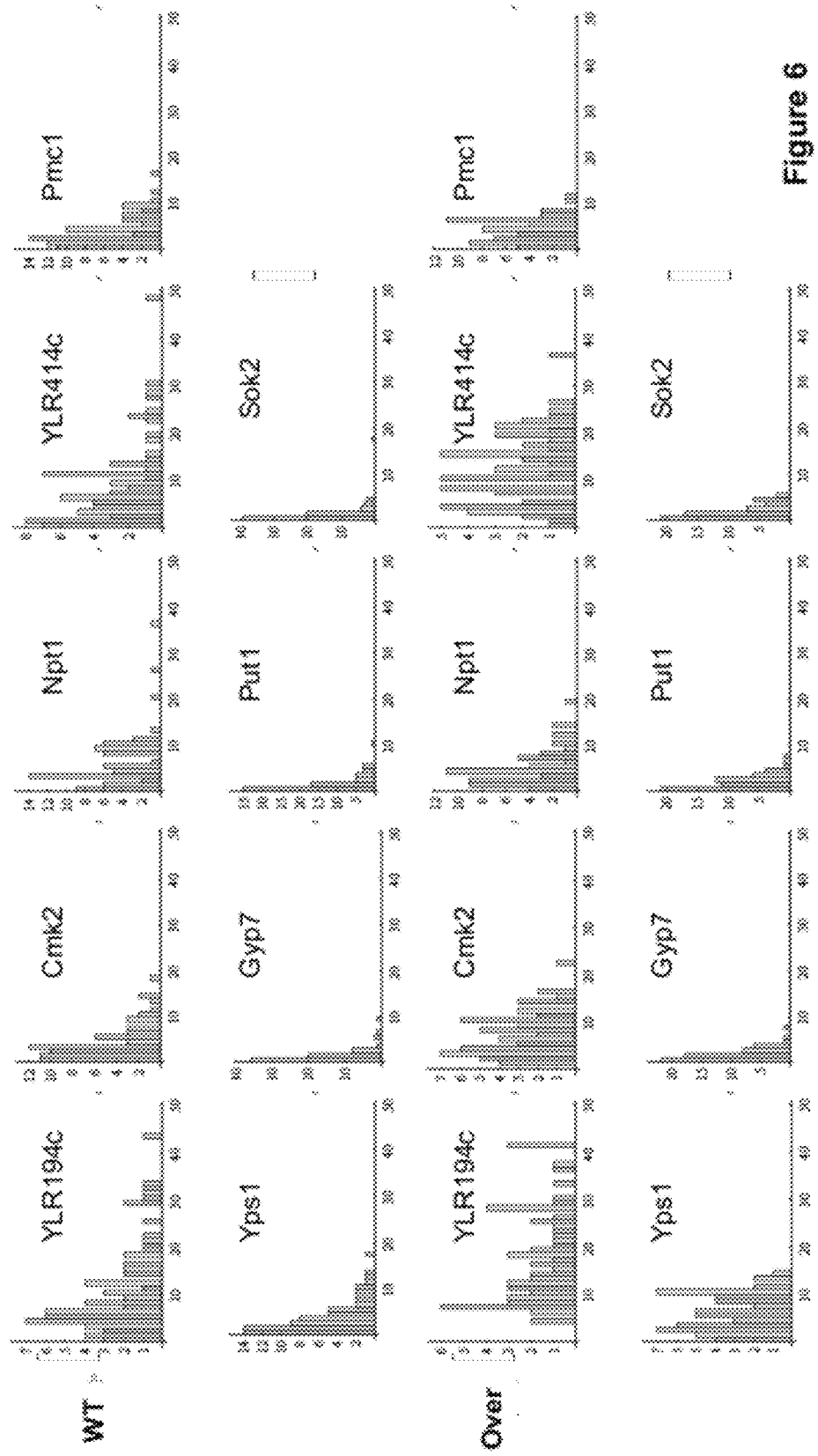
FIG. 6 depicts an exemplary embodiment, showing the distribution of target mRNA copy number in single cells (Wt vs Crz1 over-expressed).

Thus the most likely mechanism for the extension of mRNA is by physical compression of the cells as they are sandwiched between coverslips during imaging. As the mRNAs are held in place by ribosomes fixed to the cellular matrix, a flattening of the cells creates a shear flow within the cells that moves the ribosomes and stretches the mRNA out in the lateral direction (FIGS. 5 and 6). Another possible explanation is that hybridized mRNAs are stiff and compression of the cell merely flattens the mRNA in the xy direction. However, given the persistence length of double stranded DNA is 150 nt and that a hybridized mRNA resembles a nicked RNA-DNA hybrid rather than a full double stranded molecule, it is unlikely that hybridized mRNA is already extended. This possibility can be ruled out with axially resolved STORM by incorporating a cylindrical lens in our setup. However, the axial resolution of the approach is 50 nm, insufficient to further resolve the typical 20-50 nm distance between the barcode positions. Compression of fixed embryos is routinely used to decrease the sectioning thickness for imaging in FISH experiments. Thus, such physical compression of the sample may serve the purpose of extending mRNAs for the barcode resolution.

Example 6

Barcoding Multiple mRNA Transcripts in Yeast

To demonstrate the feasibility of this approach, multiple mRNAs species in single *Saccharomyces cerevisiae* cells were detected using the methods and system described herein. The current methods and system differ from the single molecule FISH (smFISH) techniques. Instead of detecting each mRNA with 40 20 mer oligonucleotide probes labeled with the same fluorophore as in smFISH, a nanoscopic barcode was imparted on each transcript by hybridizing probes labeled in different fluorophores in a spatially ordered fashion. The current SRM resolution of 15 nm allows a code region of 50 bp long to be resolved. Different species of mRNA can be uniquely barcoded and quantitated by tabulating barcodes in individual cells (FIG. 1). Previous works in multiplex FISH rely on using intensity ratio of fluorophores to label distinct chromosomal loci, and transcriptional active sites. The current approach spatially barcodes single mRNAs in a 5' to 3' fashion, allowing potentially limitless capacity for multiplexing and the spatial capacity to accommodate all transcripts in the cell.

Figure 2:
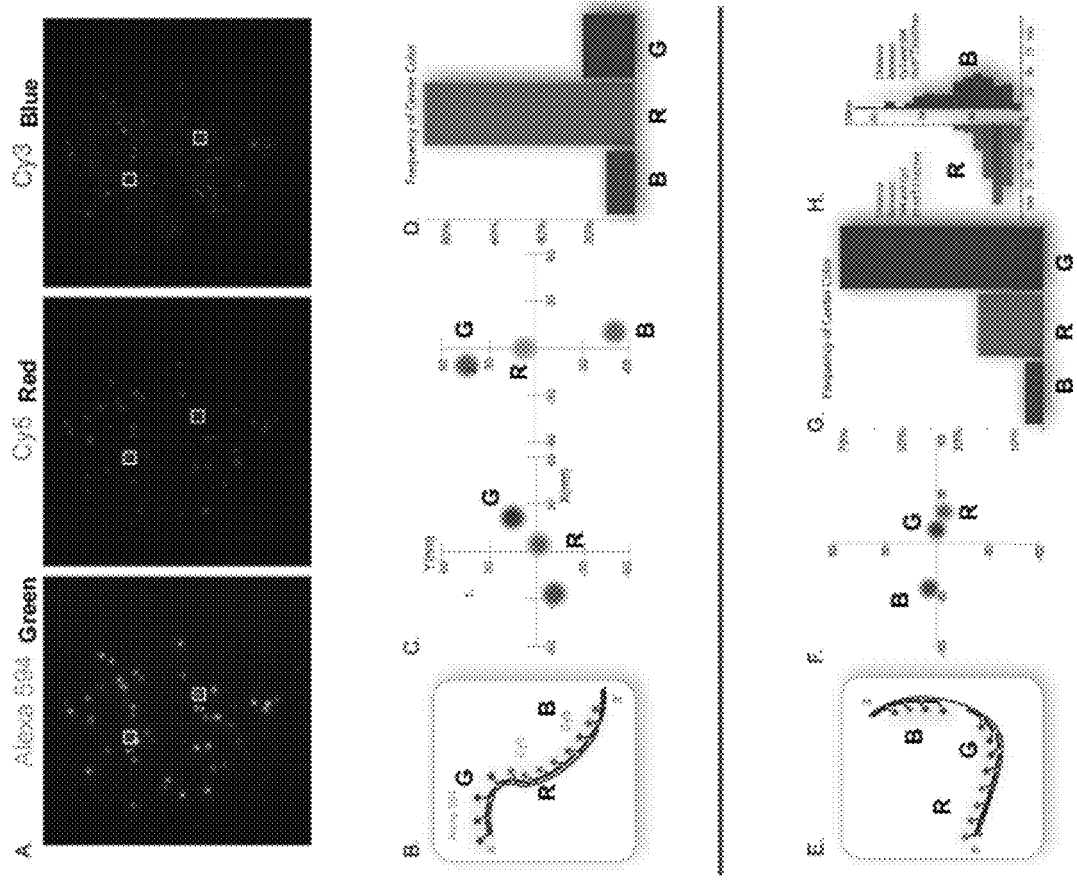
FIGS. 7A, 7A-1, 7A-2, 7B, 7B-1 and 7B-2 depict an exemplary embodiment, showing Single cell in Total Internal Reflection Fluorescence Microscope (TIRFM) imaging and Stochastical Optical Resonstruction Microscopy (STORM) reconstruction.

It was first demonstrated that barcodes on mRNAs can be resolved spatially, using Fluorescence Imaging with One-Nanometer Accuracy (FIONA). Twelve oligo probes targeting GFP mRNA were grouped in sets of 4 and labeled by 3 different fluorophores. In hybridized yeast cells, target mRNA appeared as co-localized, near-diffraction limited, spots in the fluorescence channels. 99±2% of spots co-localized in all three channels and each spot typically consists of 2.7±1 probes, as determined by photobleaching (SOM). These results suggested that hybridization is 70±10% efficient and single labeled probes can be readily detected. The centroid positions of the probes can be determined accurately by Gaussian fitting, with a localization accuracy of ~5 nm (with ~104 photons) with an error of ~5 nm due to chromatic aberration in our imaging setup (SOM). Following center-of-mass image alignment, we observe the correct spatial order in 80±10% of the labeled mRNAs, with the average spatial separation of 25±10 nm between centroids (FIG. 2a). The spatial distances is shorter than the 40 nm expected for a fully extended 120 bp region of hybridized mRNA, but significantly more than the potentially folded native structure of the mRNA. It was hypothesized that a partially stretched mRNAs is observed because as the cells are sandwiched between 2 glass coverslips for imaging, the compression of the cells generates a shear flow acting on the ribosomes attached to the mRNA, resulting in extension of the mRNA in the planar direction. This extension of the mRNAs from their native conformation allows the 80% fidelity in reading out the barcodes.

To demonstrate the robustness of the FIONA barcode technique, the order the fluorophore labeling was switched and the distances between 2 barcode positions was increased. The corresponding switch was observed in the ordering of the centroids (FIG. 2b) with 70±10% correct ordering as well as the lengthening of the distances between the barcode positions (from 25 nm to 40±10 nm). In addition, mRNAs of different length from 700 bp to 14 kb were labeled using this method, without observing significant differences in the detection of the correct ordering of the barcode. The FIONA approach is easy to implement with conventional fluorophores and has high localization accuracy. However, the approach is limited in labeling density by diffraction and prevents repeat usage of colors for coding. For example, a RGR coding scheme cannot be resolved by FIONA, as the two red positions are within the same diffraction limited volume. To circumvent both problems, photoswitchable fluorophores were used to label the oligonucleotide probes.

A barcode from photoswitchable dyes labeled oligos based upon the Cy5 dye-pairs were used. In the STORM experiment, an activator dye (Alexa405, Alexa488, or Cy3) were placed in close proximity (~1 nm) to the switchable dye (Cy5, Cy5.5 or Cy7). As Cy5 is imaged and switched off by a 640 nm laser, it can be stochastically re-activated by weak illumination in the activator dye wavelength. Three activator dyes can be paired with three emitter dyes to provide at 9 colors in STORM. The probes were designed such that two probes, one labeled in its 3' position with the activator and the other in 5' position with the Cy5 emitter dye (FIG. 3a), were hybridized on the mRNA at adjacent positions separated by 2 bp, bring the dye pairs within 1 nm. As both probes are required for the fluorophore to be re-activated, non-specifically bound Cy5 probes in the cell cannot be reactivated after the initial switching off step. In contrast, directly labeling oligos with Cy3-Cy5 covalently-linked pairs will have the same non-specific background as standard FISH and have drastically increased blinking rate.

Since the images were all acquired in the Cy5 channel, there is no need for chromatic aberration corrections. Three color barcodes (FIG. 3a) can be reconstructed from the super-resolution movies and the correct order resolved 70±10% of the times independent of mRNAs species (FIGS. 3b and 3c). In addition, colors could be used repeatedly, i.e., RGR, (FIG. 3d), which in principle allows limitless number of unique barcodes. Given the typical size of the barcodes (100 nm), a typical yeast cell with a diameter of Sum can accommodate >100,000 barcoded transcripts per cell, comparable to the size of the yeast transcriptome.

Practically, the accurate readout of barcode is constrained by the hybridization efficiency and non-specific blinking of the Cy5 dyes which distort super-resolution reconstruction. As each probe has 70% chance of hybridizing, the pairs are generated successfully 50% of times. With 4 redundant probe pairs per barcode position, the chance of having all three positions present with at least one pair of probes is 81%, consistent with our observation that 77% 3 color codes are complete. In the directly labeled probes used in the FIONA experiments, a 4 probe redundancy was sufficient to ensure that 98% of time at least one probe is bound in each channel. Thus, it was anticipated that with the development of fluorophores with improved non-specific activation rates. Thus, barcodes could be reconstructed more accurately, and oligo probes could be labeled directly to increase the chance that all the code positions are present.

The unique capabilities of the barcoding FISH approach in studying genetic networks in single cells was demonstrated by profiling a set of co-regulated genes controlled by a transcription factor Crz1. It was previously shown that Crz1 pulses in its nuclear localization in frequency-modulated fashion. However, not every Crz1 localization pulse give rise to a transcriptional burst in a particular target gene. The super-resolution barcoding approach allow us to determine whether these transcriptional bursts are uncorrelated across different target genes, suggesting intrinsic source of stochasticity at the promoter, or are correlated, suggesting extrinsic contributions. By fixing cells in conditions in which the interval between Crz1 pulses are longer than the typical mRNA lifetime, we can capture the distribution of transcriptional responses among genes to each Crz1 pulse in single cells.

Nine Crz1 target genes were chosen based on previous microarray and flow-cytometry experiments to represent a range of expression levels and loci on different chromosomes (Table 1). The transcripts were encoded analogous to Huffman coding, with the highest expressed genes assigned the least complex barcode. As our 3 color barcodes have an error rate of 20% in crosstalk to the 2 color barcodes due to hybridization efficiency, assigning the lowest expressed genes with 3 color codes diminishes the error in over-estimating the abundances of 2 color coded genes. From tabulating barcodes, the distribution of copy numbers for each gene was determined, and the pair wise correlation between target genes was calculated. Significant stochasticity was found in the expression levels for many of the genes ($CV=0.9\pm0.1$), suggesting presence of transcription bursts. In addition, we observed large variability in the pair-wise correlation between different genes, from $R=0.19\pm0.14$ to $R=0.8\pm0.07$. In genes pairs that are weakly correlated, a stark disparity in expressions is observed in >50% of cells in which some genes are clearly highly expressed with a copy number of 20-30 per cell, while others genes in the same cells are not expressed at all (FIG. 4b). It was shown that the strength of correlation is related to the promoter affinity to Crz1: promoter with high affinity for Crz1 such as NPT1 and PMC1 are more correlated compared to promoters with weaker affinities such as YLR194c and Cmk2, and are unrelated to chromosomal location (SOM). Affinity does not correlate with the expression levels of the promoter. Furthermore, we show that over-expression of Crz1 significantly improve the correlation among genes, especially among weak promoters (FIG. 4e-g). These results show that the randomness in Crz1 occupancy at the promoter is responsible for the stochastic and uncorrelated transcription bursts in the network of targets genes.

Nine genes were barcoded with each circle representing 4 pair of probes. Their abundances in individual cells are tabulated. Note the heterogeneity in expression levels within a single cell.

Figure 4H:
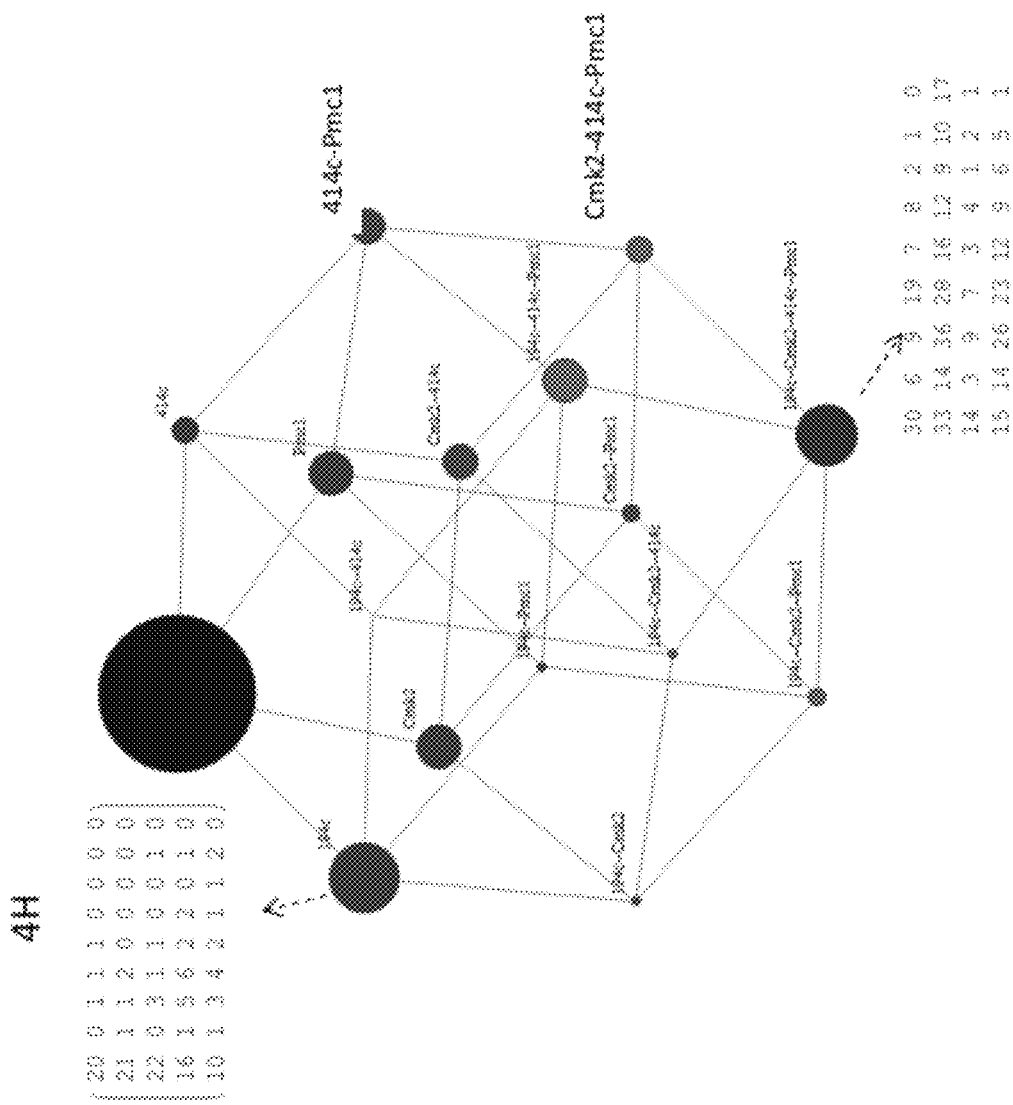

The multidimensional transcriptional dataset captured by barcoded FISH cannot be fully represented through pair-wise correlations. To present in an intuitive manner the higher order correlations in the Crz1 targets, each gene was classified as either highly and lowly expressed in a cell, thresholding on the average expression level of that gene. The states were then enumerated with a given subset of genes highly expressed and represent the probability of finding cells in that state by the size of the circle in FIG. 4H. In a projection of the dataset focusing on 4 genes for clarity, it was observed that a range of expression states is populated, but not all states are equally probable. In particular the states representing coincidences of high expressions in weak promoters have the low occurrences. While YLR414c and YLR194c are relatively well correlated in a pairwise fashion ($R=0.44\pm0.14$, FIG. 4C), cells with only both YLR414c and YLR194c highly expressed were not observed (FIG. 4H). This apparent contradiction was resolved by noting that in cells with both YLR414c and YLR194c highly expressed, the other genes Cmk2 and PMC1 were also likely to be highly expressed, occurring in $10.1\pm3.5\%$ of the cells. The same high degree of correlation was observed in $10.1\pm3.5\%$ of the cells with a larger set of genes. These results suggests an extrinsic factor, such as variations in the localization intensity of each Crz1 pulse, contributes to the higher order correlations among genes in addition to the intrinsic stochasticity at the promoters level, accounting for between 20-80% of the variations observed depending on promoter affinity.

SUper-Resolution barcode FISH(SURF) of the present invention highlights an alternative path to genome-wide transcriptional profiling in single cells. Nine genes were multiplexed by utilizing only 3 super-resolution colors, without the use of repeated barcodes (FIG. 3D), and without resolving objects in the axial direction. By incorporating an expanded palette of super-resolution fluorophores with higher localization resolution and contrast ratios, it will be possible to increase the labeling density and multiplex capability dramatically, potentially to the genome level. While much work remains, SURF has the potential to be a powerful technique and offers several distinct advantages compare to the approach of directly scaling down current high-throughput techniques to the single cell level. First, it bypasses the problems of limiting starting material and amplification error associated with working with single cells. Second, it avoids the laborious and error prone process

TABLE 1

Single cell measurements of Crz1 target genes.

|   | YLR19c (BBB) | CMK2 (GGG) | YLR414c (RRR) | NPT1 (G-B) | PMC1 (R-B) | YPS1 (R-G) | GYP7 (GRB) | PUT1 (RGB) | SOK2 (RBG) |
|---|---|---|---|---|---|---|---|---|---|
| Cell 1 | 2 | 3 | 5 | 2 | 1 | 0 | 0 | 0 | 0 |
| Cell 2 | 9 | 6 | 13 | 2 | 1 | 3 | 0 | 0 | 0 |
| Cell 3 | 14 | 6 | 8 | 4 | 1 | 4 | 1 | 2 | 1 |
| Cell 4 | 14 | 3 | 17 | 0 | 4 | 1 | 0 | 0 | 0 |
| Cell 5 | 0 | 3 | 13 | 4 | 0 | 0 | 0 | 1 | 0 |
| Cell 6 | 5 | 1 | 7 | 3 | 5 | 1 | 0 | 0 | 0 |
| Cell 7 | 11 | 7 | 9 | 8 | 3 | 4 | 0 | 2 | 3 |
| Cell 8 | 23 | 24 | 46 | 5 | 10 | 6 | 5 | 5 | 1 |
| Cell 9 | 9 | 9 | 21 | 5 | 0 | 2 | 0 | 0 | 0 |

R: Red; G: Green; B: Blue.

of isolating single cells from tissues or cell aggregates. As in situ observations retain the spatial and cellular context of genetic information, this approach has powerful applications to a large range of biological systems from biofilms to embryos where interactions among heterogeneous cellular populations play an essential role. Third, it is cost and information efficient as many cells can be imaged simultaneously under a microscope, whereas sequencing individual cells to generate a large dataset can quickly become expensive. Lastly, with the development of versatile aptmers and synthetic antibodies, SURF may be generalized to a large pool of molecules, bringing the power of omics into single cell system biology.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the specific number of antigens in a screening panel or targeted by a therapeutic product, the type of antigen, the type of cancer, and the particular antigen(s) specified. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method for detecting a single molecule of an mRNA species of interest in a single cell, comprising:
   (i) creating a molecular barcode for the single molecule of the mRNA species of interest in the single cell, comprising:
   (a) providing a plurality of different labeled probe-pairs that are specific to a single molecule of the mRNA species of interest in the single cell, wherein the probes in each probe pair of the probe-pairs comprise a nucleic acid probe labeled with a photoswitchable fluorophore and a nucleic acid probe labeled with an activator fluorophore of the photoswitchable fluorophore, wherein the photoswitchable fluorophore can be cycled between a fluorescent state and a dark state and the activator fluorophore is capable of facilitating photo-activation of the photoswitchable fluorophore at a specific wavelength, and wherein each probe in each probe pair of the probe-pairs specifically hybridizes to a different location of the mRNA species of interest, and the photoswitchable fluorophore and the activator fluorophore in each probe pair of the probe-pairs are different such that each probe pair of the probe-pairs can generate a different fluorescent signal with a different color or with a different fluorescent intensity, and
   (b) hybridizing the mRNA species of interest within the single cell with said plurality of different labeled different probe-pairs, thereby forming a complex comprising the mRNA species of interest and said plurality of different labeled probe-pairs such that the photoswitchable fluorophore and activator fluorophore of each probe pair of the probe-pairs on the complex are in sufficiently close proximity to each other, and two or more different fluorescent signals with different colors or with different fluorescent intensities are formed along the sequence of the mRNA species of interest on the complex in a spatially ordered fashion and a pattern of fluorescent signals is formed on the complex, wherein the molecular barcode is the pattern of fluorescent signals formed on the complex; and
   (ii) resolving said molecular barcode by utilizing stochastic optical reconstruction microscopy (STORM)and detecting the single molecule of the mRNA species of interest in the single cell based on analyzing said molecular barcode.

2. The method of claim 1, wherein said cell is essentially intact or undisrupted.

3. The method of claim 1, wherein said cell is a prokaryotic cell or a eukaryotic cell.

4. The method of claim 1, wherein said single cell is selected from the group consisting of a bacterium, an archaea, a protist, a fungus, a plant cell, an animal cell, a mammalian cell, a mouse cell, a human cell, a cancer cell, a blood cell, a lymphocyte, an erythrocyte, a white blood cell, an epithelial cell, a pituitary cell, a gut or respiratory tract cell, a gland cell, a thyroid gland cell, a parathyroid gland cell, a adrenal gland cell, a muscle cell, a ciliated cell, an embryonic cell, a sensory transducer cell, a neuron, a glial cell, a lens cell, a kidney cell, a pigment cell, and a pancreatic cell.

5. The method of claim 1, wherein said plurality of probes comprises oligonucleotides.

6. The method of claim 1, wherein the photoswitchable fluorophore or the activator fluorophore is selected from the group consisting of fluorescein, rhodamine, Alexa Fluors, Dy Light fluors, ATTO Dyes, and analogs or derivatives thereof.

7. The method of claim 1, wherein the photoswitchable fluorophore or the activator fluorophore is selected from the group consisting of fluorescein and chemical derivatives thereof, Eosin, Carboxyfluorescein, Fluorescein isothiocyanate (FITC), Fluorescein amidite (FAM), Erythrosine, Rose Bengal, fluorescein secreted from the bacterium Pseudomonas aeruginosa, Methylene blue, Laser dyes, Rhodamine dyes, Rhodamine, Rhodamine 6G, Rhodamine B, Rhodamine 123, Auramine 0, Sulforhodamine 101, Sulforhodamine B, Texas Red, ATTO dyes, Acridine dyes, Acridine orange, Acridine yellow, Alexa Fluor, 7-Aminoactinomycin D, 8-Anilinonaphthalene-l-sulfonate, Auramine-rhodamine stain, Benzanthrone, 5, 12-Bis(phenylethynyl)naphthacene, 9, 10 -Bis(phenylethynyl)anthracene, Blacklight paint, Brainbow, Calcein, Carboxyfluorescein, Carboxyfluorescein diacetate succinimidyl ester, Carboxyfluorescein succinimidyl ester, 1 -Chloro-9, 10-bis(phenylethynyl)anthracene, 2-Chl oro-9, 10-bi s(pheny 1 ethyny 1)anthracene, 2-Chl oro-9, 10-di pheny lanthracene, Coumarin, Cyanine dyes, Cy3, Cy5, Cy5.5, DiOC6, SYBR Green I, DAPI, Dark quencher, DyLight Fluor, Fluo-4, FluoProbes, Fluorone dyes, Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin, Fluoro-Jade stain, Fura-2, Fura-2-acetoxymethyl ester, Green fluorescent protein, Hoechst stain, Indian yellow, Indo-1, Lucifer yellow, Luciferin, Merocyanine, Optical brightener, Oxazin dyes, Cresyl violet, Nile blue, Nile red), Perylene, Phenanthridine dyes, Ethidium bromide, Propidium iodide, Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate) ruthenium(II), TSQ, Umbelliferone, and Yellow fluorescent protein.

8. The method of claim 1, wherein said fluorescent signals comprise a light at a wavelength in the visible range.

9. The method of claim 1, wherein said fluorescent signals comprise lights of different wavelengths in the visible range.

10. The method of claim 1, wherein the plurality of different labeled probe-pairs comprises 3 probe-pairs.

11. The method of claim 1, wherein the plurality of different labeled probe-pairs comprises 4 probe-pairs.

12. The method of claim 1, wherein the cell comprises at least 1000 mRNA species.

13. The method of claim 1 further comprising:
   (iii) quantifying the mRNA species of interest in said single cell.

* * * * *